United States Patent [19]

Gange

[11] Patent Number: 5,502,071
[45] Date of Patent: Mar. 26, 1996

[54] INDOLES AS INSECTICIDES AND ACARICIDES

[75] Inventor: David M. Gange, Mercer, N.J.

[73] Assignee: American Cyanamid Company, Wayne, N.J.

[21] Appl. No.: 293,152

[22] Filed: Aug. 19, 1994

[51] Int. Cl.$^6$ .................................................. A01N 43/38
[52] U.S. Cl. ........................................................ 514/415
[58] Field of Search ............................................... 514/415

[56] References Cited

U.S. PATENT DOCUMENTS

| | | | |
|---|---|---|---|
| 4,132,319 | 7/1992 | Girard et al. | 514/415 |
| 4,614,807 | 9/1986 | Flaugh | 548/507 |
| 4,812,162 | 3/1989 | Anthony et al. | 71/90 |
| 4,849,443 | 7/1989 | Tessier et al. | 514/419 |
| 5,324,547 | 8/1994 | Konya et al. | 252/380 |

FOREIGN PATENT DOCUMENTS

| | | |
|---|---|---|
| 556949A2 | 8/1993 | European Pat. Off. |
| 62-077366A2 | 4/1987 | Japan |
| 6092935A2 | 4/1994 | Japan |

OTHER PUBLICATIONS

Hiremath, S. P.; Jivanagi, A. S., Purohit, M. G., Indian J. Chem., vol. 32B, 662–7, (1993).
Andreani, A. and Rambaldi, M., Journal of Heterocyclic Chemistry, 25, 1519–23, (1988).
Ohta, T. and Somei, M., Heterocycles, vol. 29 (9), 1663–1667, (1989).
Ishibashi, H.; Mita, N.; Matusba, N.; Kubo, T.; Nakanishi, M.; Ikeda, M., Journal of Chemical Society, Perkin Translation 1 (2), 2821–2825, (1976).
Brooke, G. M.; Chambers, R. D.; Musgrave, K. R.; Storey, R. A.; Yeador, J., Ibid (21),, 2821–5 (1974).
DaSettimo, A.; Minicagli, C.; Nannipieri, E., Journal of Organic Chemistry, 39, 1995–1998, (1974).
Bourdais, J. and Lorre, A., Journal of Heterocyclic Chemistry, 12, 1111–1115, (1975).
DeRosa, M.; Carbognani, L.; Febres, A., Journal of Organic Chemsitry, 46, 2054–2059, (1981).
Kissman, H. M.; Farnsworth, D. W.; Witkop B., Journal of the American Chemical Society, 74, 3948–3949, (1952).
Hine, J. and Flachskam, Jr., R. L., Journal of Organic Chemistry, 39, 1836–1838, (1974).
Houlihan, W. J., *Heterocyclic Compounds*, vol. 25, 70–84, J. Wiley & Sons, N.Y., (1972).
Sundberg, R. J., Journal of Organic Chemistry, 30, 3604–3610, (1965).

*Primary Examiner*—Allen J. Robinson
*Attorney, Agent, or Firm*—Gregory M. Hill

[57] ABSTRACT

There are provided methods for the control of insects and the protection of crops from the damage caused thereby which comprise the use of compositions comprising an indole compound of formula I

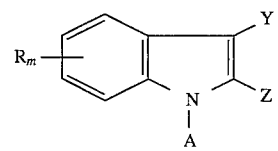

4 Claims, No Drawings

INDOLES AS INSECTICIDES AND ACARICIDES

BACKGROUND OF THE INVENTION

Significant global economic losses in major agronomic crop production are caused by the damage and infestation of insect and acarid pests. Such pest infestation can result in lower crop yields, lower crop quality, reduced consumption, increased perishability, increased risk of disease, higher processing cost, higher transportation cost and increased market prices. Crop reduction due to said insect and acarid pests, for example in cotton and peanuts, ranges as high as 39% and 78%, respectively. Therefore, new and effective insect and acarid control agents and crop protection methods are a continuing global need.

Therefore, it is an object of this invention to provide an effective method for the control of pestiferous insects and acarina.

It is another object of this invention to provide a method for the protection of growing and harvested crops from the harmful and deleterious effects caused by insect and acarid attack and infestation.

It is a further object of this invention to provide insecticidal and acaricidal compounds and compositions and methods for their preparation.

SUMMARY OF THE INVENTION

The present invention provides a method for the control of insect and acarid pests which comprises contacting said pests or their food supply, habitat or breeding grounds with a pesticidally effective amount of a compound of formula I

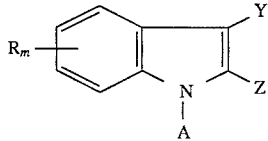
(I)

wherein R, Y and Z include electron withdrawing groups and exclude electron donating groups, A is any group capable of enzymatic or hydrolytic cleavage and m is an integer of 1, 2, 3 or 4.

The present invention also provides a method for the protection of growing crops from the attack or infestation by insect or acarid pests which comprises applying to the foliage of the plants, or to the soil, water, or other medium in which they are growing, a pesticidally effective amount of a substituted indole compound of formula I.

This invention further describes compounds, compositions comprising those compounds, and methods for preparing those compounds, which are useful as insecticidal and acaricidal agents.

DETAILED DESCRIPTION OF THE INVENTION

A wide variety of insects and acarina cause great economic loss by damaging or destroying agricultural crops and horticultural and pharmaceutical plants; by aiding in the spread and development of bacteria, fungi and viruses that produce diseases of plants; and by destroying or devaluing stored foods, or other plant products and possessions. Insect and acarid attack and infestation cause some of the farmers' greatest problems the world over. The need for alternative and effective insect and acarid control is a continuing global concern.

It has now been found that the substituted indole compounds of formula I are highly effective agents for the control of a wide variety of insect and acarid pests.

The formula I indole compounds of the present invention include those which have the structural formula

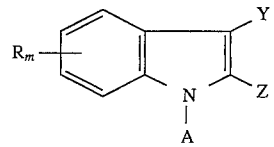

wherein R, Y and Z include electron withdrawing groups and exclude electron donating groups, A is any group capable of enzymatic or hydrolytic cleavage and m is an integer of 1, 2, 3 or 4.

In particular, the indole compounds of the present invention include those formula I compounds wherein Y and Z are each independently hydrogen, halogen, CN, $NO_2$, $S(O)_nR_1$, $C_1$-$C_6$haloalkyl, $C_1$-$C_6$haloalkoxy, $COR_2$, $CSR_3$, or W, with the proviso that only one of Y or Z may be W, and with the further proviso that only one of Y or Z may be hydrogen;

W is

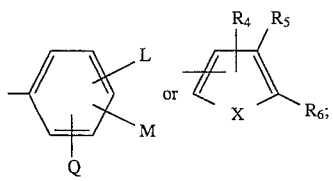

R is any combination of from one to four halogen, CN, $NO_2$, $S(O)_nR_7$, $C_1$-$C_6$haloalkyl or $C_1$-$C_6$haloalkoxy;

m is an integer of 1, 2, 3 or 4;

n is an integer of 0, 1, or 2;

L, M and Q are each independently hydrogen, halogen $NO_2$, CN, $C_1$-$C_4$haloalkyl, $C_1$-$C_4$haloalkoxy, $COR_7$ or $S(O)_nR_8$;

$R_1$, $R_2$, $R_3$, $R_7$ and $R_8$ are each independently $C_1$-$C_6$ haloalkyl;

X is O or S;

$R_4$, $R_5$ and $R_6$ are each independently hydrogen, halogen, $NO_2$, CN, $S(O)_nR_9$ or $R_5$ and $R_6$ may be taken together with the atoms to which they are attached to form a ring in which $R_5R_6$ is represented by the structure

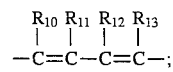

$R_{10}$, $R_{11}$, $R_{12}$ and $R_{13}$ are each independently hydrogen, halogen, CN, $NO_2$ or $S(O)_nR_{14}$;

$R_9$ and $R_{14}$ are each independently $C_1$-$C_6$ haloalkyl;

A is $R_{15}$, $OR_{15}$ or CN;

$R_{15}$ is hydrogen, $COR_{16}$, $CHR_{17}NHCOR_{18}$, $CH_2SQ_1$,

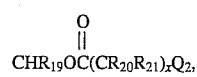

$C_1$-$C_6$alkyl optionally substituted with
one to three halogen atoms,
one tri($C_1$-$C_4$ alkyl)silyl,
one hydroxy,
one cyano,
one or two $C_1$-$C_4$ alkoxy groups optionally substituted with one to three halogen atoms, one $C_1$–$C_4$ alkylthio, one phenyl optionally substituted with one to three halogen atoms, one to three $C_1$–$C_4$ alkyl groups or one to three $C_1$–$C_4$ alkoxy groups, one phenoxy group optionally substituted with one to three halogen atoms, one to three $C_1$–$C_4$ alkyl groups or one to three $C_1$–$C_4$ alkoxy groups, one benzyloxy group optionally substituted on the phenyl ring with one to three halogen atoms, one to three $C_1$–$C_4$ alkyl groups or one to three $C_1$–$C_4$ alkoxy groups, one $C_1$–$C_6$ alkylcarbonyloxy group optionally substituted with one to three halogen atoms, one $C_2$–$C_6$ alkenylcarbonyloxy group optionally substituted with one to three halogen atoms, one phenylcarbonyloxy group optionally substituted with one to three halogen atoms, one to three $C_1$–$C_4$ alkyl groups or one to three $C_1$–$C_4$ alkoxy groups, one $C_1$–$C_6$ alkoxycarbonyl group optionally substituted with one to three halogen atoms or one to three $C_1$–$C_4$ alkoxy groups, or one benzylcarbonyloxy group optionally substituted on the phenyl ring with one to three halogen atoms, one to three $C_1$–$C_4$ alkyl groups or one to three $C_1$–$C_4$ alkoxy groups, $C_3$–$C_6$ alkenyl optionally substituted with one to three halogen atoms or one phenyl group or $C_3$–$C_6$ alkynyl optionally substituted with one to three halogen atoms or one phenyl group;

$R_{16}$ is $C_1$–$C_6$ alkyl or $C_3$–$C_6$ cycloalkyl each optionally substituted with one to three halogen atoms, one hydroxy, one cyano, one or two $C_1$–$C_4$ alkoxy groups optionally substituted with one to three halogen atoms, one $C_1$–$C_4$ alkylthio, one phenyl group optionally substituted with one to three halogen atoms, one to three $C_1$–$C_4$ alkyl groups or one to three $C_1$–$C_4$ alkoxy groups, one phenoxy group optionally substituted with one to three atoms, one to three $C_1$–$C_4$ alkyl groups or one to three $C_1$–$C_4$ alkoxy groups, one benzyloxy group optionally substituted on the phenyl ring with one to three $C_1$–$C_4$ alkyl groups or one to three halogen atoms, one to three $C_1$–$C_4$ alkoxy groups, one $C_1$–$C_6$ alkylcarbonyloxy group optionally substituted with one to three halogen atoms, one $C_2$–$C_6$ alkenylcarbonyloxy group optionally substituted with one to three halogen atoms, one phenylcarbonyloxy group optionally substituted with one to three halogen atoms, one to three $C_1$–$C_4$ alkyl groups or one to three $C_1$–$C_4$ alkoxy groups, one $C_1$–$C_6$ alkoxycarbonyl group optionally substituted with one to three halogen atoms or one to three $C_1$–$C_4$ alkoxy groups, or one benzylcarbonyl group optionally substituted on the phenyl ring with one to three halogen atoms, one to three $C_1$–$C_4$ alkyl groups or one to three $C_1$–$C_4$ alkoxy groups, $C_2$–$C_6$ alkenyl optionally substituted with one to three halogen atoms or one phenyl group, $C_3$–$C_6$ alkynyl optionally substituted with one to three halogen atoms or one phenyl group, phenyl optionally substituted with one or more halogen, $C_1$–$C_4$ alkyl, $C_1$–$C_4$ alkoxy, phenoxy, $C_1$–$C_4$ alkylthio, tri($C_1$–$C_4$ alkyl)silyl, $C_1$–$C_4$ alkylsulfinyl, $C_1$–$C_4$ alkylsulfonyl, CN, $NO_2$ or $CF_3$ groups, phenoxy optionally substituted with one or more halogen, $C_1$–$C_4$ alkyl, $C_1$–$C_4$ alkoxy, $C_1$–$C_4$ alkylthio, tri($C_1$–$C_4$ alkyl)silyl, $C_1$–$C_4$ alkylsulfinyl, $C_1$–$C_4$ alkylsulfonyl, CN, $NO_2$ or $CF_3$ groups, 1- or 2-naphthyl, 2-, 3-, or 4-pyridyl optionally substituted with halogen, $C_1$–$C_6$ alkoxy optionally substituted with halogen, or $C_2$–$C_6$ alkenyloxy optionally substituted with halogen;

$R_{17}$ is hydrogen or $C_1$–$C_4$ alkyl;

$R_{18}$ is $C_1$–$C_6$ alkyl, $C_1$–$C_6$ haloalkyl, $C_1$–$C_6$ alkoxy, $C_1$–$C_6$ haloalkoxy, phenyl optionally substituted with halogen, CN, $NO_2$, $C_1$–$C_4$ alkyl, $C_1$–$C_4$ alkoxy or $CF_3$, 2- or 3-thienyl, or 2- or 3- furyl;

$Q_1$ is

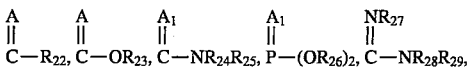

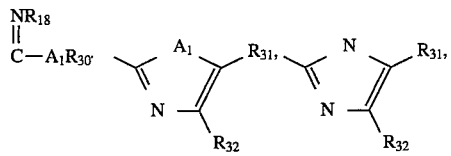

CN, $C_1$–$C_6$ alkyl optionally substituted with halogen, CN or phenyl group, or phenyl optionally substituted with one or more halogen, $C_1$–$C_4$ alkyl, $C_1$–$C_4$ alkoxy, CN, $NO_2$, $CF_3$ or $NR_{33}R_{34}$;

$A_1$ is O or S;

$R_{22}$ is $C_1$–$C_6$ alkyl or phenyl;

$R_{23}$ is $C_1$–$C_6$ alkyl;

$R_{24}$ and $R_{25}$ are each independently hydrogen, $C_1$–$C_6$ alkyl or may be taken together with the atom to which they are attached to form a 5- to 7-membered ring;

$R_{26}$ is $C_1$–$C_4$ alkyl;

$R_{27}$ is hydrogen, $C_1$–$C_4$ alkyl or may be taken together with either $R_{28}$ or $R_{29}$ and the atoms to which they are attached to form a 5- to 7-membered ring optionally substituted with one or two $C_1$–$C_4$ alkyl groups;

$R_{28}$ and $R_{29}$ are each independently hydrogen or $C_1$–$C_4$ alkyl;

$R_{30}$ is $C_1$–$C_4$ alkyl or when taken together with $R_{27}$ and the atoms to which they are attached may form a 5- to 7-membered ring optionally substituted with one or two $C_1$–$C_4$ alkyl groups;

$R_{31}$ and $R_{32}$ are each independently hydrogen, $C_1$–$C_4$ alkyl or when taken together may form a ring wherein $R_{31}R_{32}$ is represented by —CH=CH—CH=CH—;

$R_{33}$ and $R_{34}$ are each independently hydrogen or $C_1$–$C_4$ alkyl;

$R_{19}$ is hydrogen or $C_1$–$C_4$ alkyl;

$R_{20}$ and $R_{21}$ are each independently hydrogen, $C_1$–$C_6$ alkyl optionally substituted with halogen, $C_1$–$C_6$ alkoxy optionally substituted with halogen, $C_1$–$C_6$ alkylthio optionally substituted with halogen, or phenyl optionally substituted with halogen, $NO_2$, CN, $C_1$–$C_4$ alkyl optionally substituted halogen, or $C_1$–$C_4$ alkoxy optionally substituted with halogen, or when $R_{20}$ and $R_{21}$ are taken together with the atom to which they are attached may form a $C_3$–$C_6$ cycloalkyl group optionally substituted with $C_1$–$C_4$ alkyl, $C_2$–$C_6$ alkenyl or phenyl, or $R_{20}$ or $R_{21}$ may be taken together with $R_{35}$ and the atoms to which they are attached to form a 4- to 7-membered heterocyclic ring;

x is an integer of 0, 1, 2, 3 or 4;

$Q_2$ is $A_2R_{35}$, $$\underset{\parallel}{P}-(OR_{36})_2,$$

$NR_{37}R_{38}$, $CR_{39}R_{40}$, $COR_{41}$, or
$C_3$–$C_6$ cycloalkyl optionally substituted with one or more $C_1$–$C_6$ alkyl, $C_2$–$C_6$ alkenyl, or
phenyl optionally substituted with halogen, $NO_2$, CN, $C_1$–$C_4$ alkyl, $C_1$–$C_4$ haloalkyl, $C_1$–$C_4$ alkoxy, or $C_1$–$C_4$ haloalkoxy;

$A_2$ is O or S(O)p;

p is an integer of 0, 1 or 2;

$R_{35}$ is hydrogen, $C_1$–$C_6$ alkyl, $C_2$–$C_6$ alkenyl, $C_2$–$C_6$ alkynyl, phenyl optionally substituted with halogen, $NO_2$, CN,
$C_1$–$C_4$ alkyl optionally substituted with halogen,
$C_1$–$C_4$ alkoxy optionally substituted with halogen,
$COR_{42}$ provided p is 0,
$COR_{43}$ provided p is 0,
$(CH_2CH_2O)_qR_{44}$, or $$\underset{N}{\overset{A_3}{\diagup}} \underset{R_{46}, \text{ or}}{\overset{R_{45}}{\diagdown}}$$

$R_{35}$ may be taken together with either $R_{20}$ or $R_{21}$ and the atoms to which they are attached to form a 4- to 7-membered heterocyclic ring;

$A_3$ is O or S;

$R_{42}$ and $R_{44}$ are each independently $C_1$–$C_6$ alkyl, $C_2$–$C_6$ alkenyl, $C_2$–$C_6$ alkynyl, or
phenyl optionally substituted with halogen, $NO_2$, CN, $C_1$–$C_4$ alkyl optionally substituted with halogen, or $C_1$–$C_4$ alkoxy optionally substituted with halogen;

q is an integer of 1, 2 or 3;

$R_{43}$ is $OR_{47}$ or $NR_{48}R_{49}$;

$R_{47}$ is $C_1$–$C_6$ alkyl or
phenyl optionally substituted with halogen, $NO_2$, CN, $C_1$–$C_4$ alkyl optionally substituted with halogen, or $C_1$–$C_4$ alkoxy optionally substituted with halogen;

$R_{48}$ and $R_{49}$ are each independently hydrogen or $C_1$–$C_4$ alkyl;

$R_{45}$ and $R_{46}$ are each independently hydrogen or $C_1$–$C_4$ alkyl, or when taken together may form a ring wherein $R_{45}R_{46}$ is represented by —CH=CH—CH=CH—;

$R_{36}$ is $C_1$–$C_4$ alkyl;

$R_{37}$ is hydrogen, $C_1$–$C_6$ alkyl, $C_2$–$C_6$ alkenyl, $C_2$–$C_6$ alkynyl, or
phenyl optionally substituted with halogen, $NO_2$, CN, $C_1$–$C_4$ alkyl optionally substituted with halogen, or $C_1$–$C_4$ alkoxy optionally substituted with halogen, or $R_{37}$ may be taken together with either $R_{20}$ or $R_{21}$ and the atoms to which they are attached to form a 4- to 7-membered heterocyclic ring;

$R_{38}$ is hydrogen, $C_1$–$C_6$ alkyl, $C_2$–$C_6$ alkenyl, $C_2$–$C_6$ alkynyl,
phenyl optionally substituted with halogen, $NO_2$, CN, $C_1$–$C_4$ alkyl optionally substituted with halogen, or $C_1$–$C_4$ alkoxy optionally substituted with halogen,

CN, $SO_2R_{51}$ or $COCHR_{52}NHR_{53}$;

$A_4$ is O or S;

$R_{50}$ is $OR_{54}$, $CO_2R_{55}$, $NR_{56}R_{57}$,
$C_1$–$C_6$ alkyl optionally substituted with halogen,
$C_2$–$C_6$ alkenyl, $C_2$–$C_6$ alkynyl or
phenyl optionally substituted with halogen, $NO_2$, CN, $C_1$–$C_4$ alkyl optionally substituted with halogen, or $C_1$–$C_4$ alkoxy optionally substituted with halogen;

$R_{54}$ and $R_{55}$ are each independently $C_1$–$C_6$ alkyl optionally substituted with one phenyl group, or
phenyl optionally substituted with halogen, $NO_2$, CN, $C_1$–$C_4$ alkyl optionally substituted with halogen, or $C_1$–$C_4$ alkoxy optionally substituted with halogen;

$R_{56}$ and $R_{57}$ are each independently hydrogen or $C_1$–$C_4$ alkyl;

$R_{51}$ is $NR_{58}R_{59}$, $C_1$–$C_6$ alkyl, $C_2$–$C_6$ alkenyl, $C_2$–$C_6$ alkynyl, or
phenyl optionally substituted with halogen, $NO_2$, CN, $C_1$–$C_4$ alkyl optionally substituted with halogen, or $C_1$–$C_4$ alkoxy optionally substituted with halogen;

$R_{58}$ and $R_{59}$ are each independently hydrogen or $C_1$–$C_4$ alkyl;

$R_{52}$ is hydrogen, $C_1$–$C_4$ alkyl optionally substituted with hydroxy, $SR_{60}$, $CONH_2$, $NH_2$,
NHC(=NH)$NH_2$, $CO_2H$,
phenyl optionally substituted with hydroxy,
3-indolyl or
4-imidazolyl;

$R_{60}$ is hydrogen or $C_1$–$C_4$ alkyl;

$R_{53}$ is $$\underset{CR_{61}}{\overset{A_{14}}{\parallel}};$$

$R_{61}$ is $C_1$–$C_6$ alkyl optionally substituted with halogen, $C_1$–$C_6$ alkoxyalkyl, $C_1$–$C_6$ alkylthio,
phenyl optionally substituted with halogen, $NO_2$, CN, $C_1$–$C_4$ alkyl optionally substituted with halogen, or $C_1$–$C_4$ alkoxy optionally substituted with halogen, $OR_{54}$, $CO_2R_{55}$ or $NR_{56}R_{57}$;

$R_{39}$ and $R_{40}$ are each independently hydrogen,
$C_1$–$C_6$ alkyl optionally substituted with halogen,
$C_1$–$C_6$ alkoxy optionally substituted with halogen,
$C_1$–$C_6$ alkylthio optionally substituted with halogen,
phenyl optionally substituted with halogen, CN, $NO_2$,
$C_1$–$C_4$ alkyl optionally substituted with halogen, or $C_1$–$C_4$ alkoxy optionally substituted with halogen, or
when $R_{39}$ and $R_{40}$ are taken together with the atom to which they are attached may form a $C_3$–$C_6$ cycloalkyl ring optionally substituted with $C_1$–$C_4$ alkyl, $C_2$–$C_6$ alkenyl or phenyl;

$R_{41}$ is $OR_{62}$, $NR_{58}R_{59}$, $C_1$–$C_4$ alkyl or
phenyl optionally substituted with halogen, CN, $NO_2$, $C_1$–$C_4$ alkyl optionally substituted with halogen, or $C_1$–$C_4$ alkoxy optionally substituted with halogen;

$R_{62}$ is $C_1$–$C_4$ alkyl or
phenyl optionally substituted with halogen, CN, $NO_2$, $C_1$–$C_4$ alkyl optionally substituted with halogen, or $C_1$–$C_4$ alkoxy optionally substituted with halogen.

The term halogen as used in the specification and claims designates chlorine, fluorine, bromine or iodine. The term haloalkyl designates an alkyl group, $C_nH_{2n+1}$ which contains from one halogen atom to $2n+1$ halogen atoms wherein the halogen atoms may be the same or different.

It is contemplated, that A may be any group that is capable of enzymatic or hydrolytic cleavage and Y, Z and R may be any combination of from 2 to 6 electron withdrawing groups that are also lipophilic. Suitable electron withdrawing groups include halogen, nitro, cyano, trifluoromethylsulfonyl, trifluoroacetyl, and the like.

Preferred compounds of the invention are those compounds of formula I wherein Y and Z are each independently hydrogen, halogen, CN, $NO_2$, $S(O)_nR_1$, $C_1$–$C_6$ haloalkyl or $C_1$–$C_6$ haloalkoxy provided only one of Y or Z is hydrogen; m is 3 or 4 and n is 1 or 2.

Also preferred are those compounds wherein Y is hydrogen, CN, $NO_2$, $S(O)_nR_1$, $C_1$–$C_6$ haloalkyl or $C_1$–$C_6$ haloalkoxy or $C_1$–$C_6$ haloalkyl and Z is phenyl optionally substituted with L, M, Q.

More preferred compounds are those compounds of formula I wherein Y is CN, $C_1$–$C_6$ haloalkyl or $SO_2R_1$ and Z is $C_1$–$C_6$ haloalkyl, $SO_2R_1$, or phenyl optionally substituted with L, M, Q.

Compounds of formula I wherein Y or Z is $C_1$–$C_6$ haloalkyl may be prepared by literature procedures such as that described by Y. Kobayashi et al in the Journal of Organic Chemistry 39, 1836 (1974) or by the reaction of the appropriate haloprecursor of formula II (wherein the halogen is I) with a $C_1$–$C_6$haloalkylcarboxylate salt or ester and copper (I) halide as shown in flow diagram I wherein the $C_1$–$C_6$haloalkylcarboxylate is sodium trifluoroacetate.

Flow Diagram I

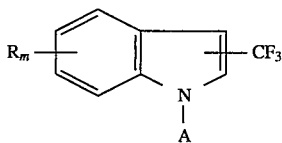

(II)

-continued
Flow Diagram I

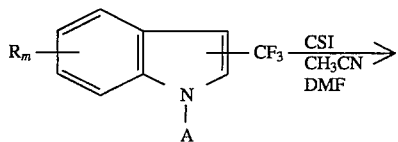

Compounds of formula I wherein Y or Z are CN may be prepared by reacting the above-prepared haloalkyl intermediate with chlorosulfonylisocyanate (CSI) in the presence of acetonitrile and dimethylformamide (DMF) as shown in flow diagram II.

Flow Diagram II

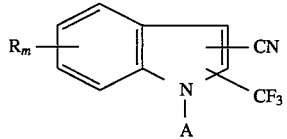

Compounds of formula I wherein Z is $S(O)_nR_1$ may be prepared from the appropriate indolenethione precursor of formula III by reaction with a suitable halogenated alkene such as chlorotrifluoroethylene in the presence of a base to give the formula I products wherein n is 0. This haloalkylthio compound may then be oxidized in the usual manner to yield the sulfone and sulfoxide analogs as shown in diagram III.

Flow Diagram III

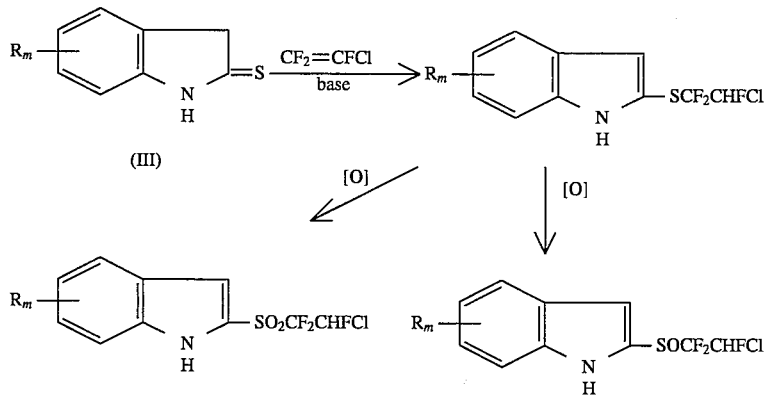

Alternatively, compounds of formula I wherein Y or Z is $S(O)_nR_1$, may be prepared by reacting the appropriate indole precursor with haloalkylsulfenyl chloride and, if desired, oxidizing the haloalkylthio indole as shown above. The reaction sequence is shown in flow diagram IV.

Flow Diagram IV

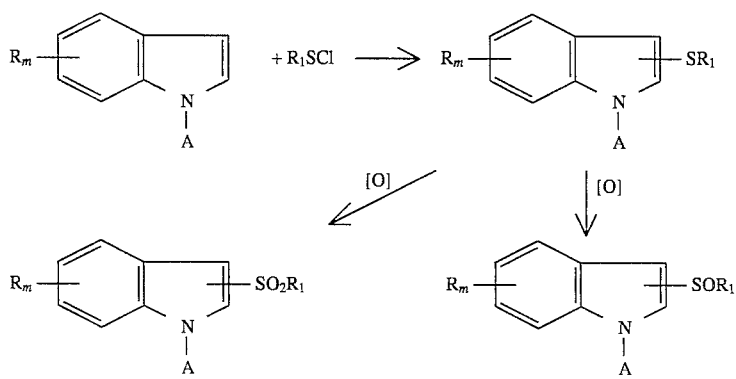

Compounds of formula I wherein Z is W may be prepared by the cyclization of the appropriate aryl hydrazone of phenyl (or substituted phenyl) hydrazine with polyphosphoric acid (PPA). For example, when W is phenyl, the hydrazone of formula IV is cyclized as shown in flow diagram V.

Flow Diagram V

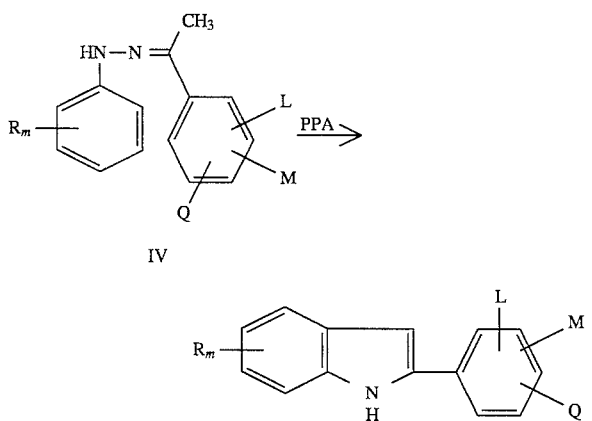

Formula I compounds wherein A is other than hydrogen may be prepared by reacting the NH indole precursor with the appropriate alkyl or carbonyl halide in the presence of a base to give products of formula I as shown in flow diagram VI.

Flow Diagram VI

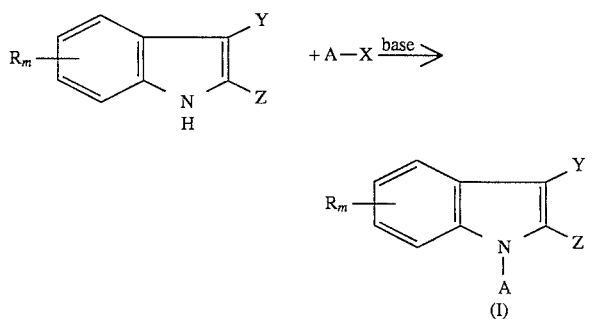

The formula I products wherein Y or Z or R are halogen or $NO_2$ may be obtained by standard halogenation or nitration procedures known in the art. These and other methods for the preparation of substituted indole derivatives of formula I will become apparent from the examples set forth below.

Substituted formula I indoles and the N-substituted derivatives thereof are effective for the control of insect and acarid pests and for the protection of growing and harvested plants and crops from attack and infestation by said pests.

In practice, generally about 10 ppm to 10,000 ppm, preferably about 100 to 5,000 ppm of the formula I compound dispersed in an agronomically acceptable liquid carrier, when applied to the plants or the soil, water, or other medium in which they are growing, is effective to protect the plants from insect and acarina attack and infestation. Applications, such as spray applications, of compositions of the invention are generally effective at rates which provide about 0.125 kg/ha to about 250 kg/ha, preferably about 1 kg/ha to 200 kg/ha, most preferably about 10 kg/ha to 100 kg/ha of active ingredient. Of course, it is contemplated that higher or lower rates of application of the substituted indole derivatives may be used depending upon the prevailing environmental circumstances such as population density, degree of infestation, stage of plant growth, soil conditions, weather conditions and the like.

Advantageously, the formula I compounds may be used in conjunction with, or in combination with, other biological and chemical control agents including other insecticides, nematicides, acaricides, molluscides, fungicides and bactericides such as nuclear polyhedrosis viruses, pyrroles, arylpyrroles, halobenzoylureas, pyrethroids, carbamates, phosphates, and the like.

Typical formulations suitable for the formula I indole derivatives are granular compositions, flowable compositions, wettable powders, dusts, microemulsions, emulsifiable concentrates and the like. All compositions which lend themselves to soil, water and foliage application and provide effective plant protection are suitable. Compositions of the invention include the formula I substituted indole derivative admixed with an agronomically acceptable inert solid or liquid carrier.

Where compositions of the invention are to be employed in combination treatments with other biological or chemical agents, the composition may be applied as an admixture of the components or may be applied sequentially. While not required, the combination composition comprising a formula I compound and a co-pesticide may also comprise other components, for example, fertilizers, inert formulation aides such as surfactants, emulsifiers, wetting agents, defoamers, dyes, extenders and the like.

For a more clear understanding of the invention, specific examples thereof are set forth below. The invention described and claimed herein is not to be limited in scope by these merely illustrative examples. Indeed, various modifications of the invention in addition to those exemplified and described herein will become apparent to those skilled in the art from the following examples and the foregoing description. Such modifications are also intended to fall with in the scope of the appended claims. The terms $^1H$, $^{13}C$, $^{19}FNMR$ designate proton, carbon and fluorine nuclear magnetic resonance (NMR) spectroscopy, respectively. IR designates infrared spectroscopy, and GC and TLC designate gas chromatography and thin layer chromatography, respectively.

EXAMPLE 1

Preparation of 2-(Trifluoromethyl)indole

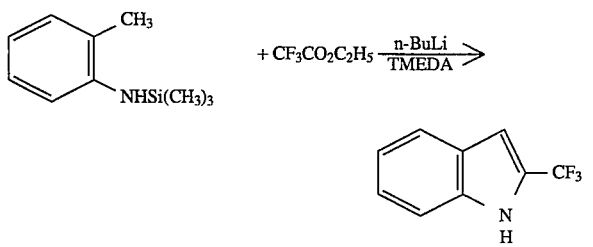

A 2.5M solution of n-butyl lithium in hexanes (8.8 mL, 22 mmole) at room temperature, under $N_2$, is treated with N,N,N',N'-tetramethylethylenediamine (TMEDA) (3.3 mL, 22 mole), stirred at room temperature for 0.5 hour, treated with N-trimethylsilyl-o-toluidine (1.79 g, 10 mmole), heated at reflux temperature for 6 hours, cooled to −78° C., treated with ethyl trifluoroacetate (1.4 mL, 12 mmole) stirred at −78° C. for 0.25 hour, warmed to room temperature, diluted with water and extracted with diethyl ether. The combined extracts are washed sequentially with 1N HCl and saturated $NaHCO_3$, dried over $MgSO_4$ and concentrated in vacuo to give a residue. The residue is chromatographed using silica gel and 4:1 hexanes:ethyl acetate as eluent to afford the title product as a light yellow solid, mp 104°–106° C. (literature mp 102° C.[1]), 0.81 g (47% yield), further identified by IR, $^1HNMR$ and $^{19}FNMR$ analyses.

[1] Y. Kobayashi, I. Kumadaki, Y. Hirose and Y. Hanazawa, Journal of Organic Chemistry, 39, 1836 (1974).

EXAMPLE 2

Preparation of N-Methyl-2-(trifluoromethyl)indole

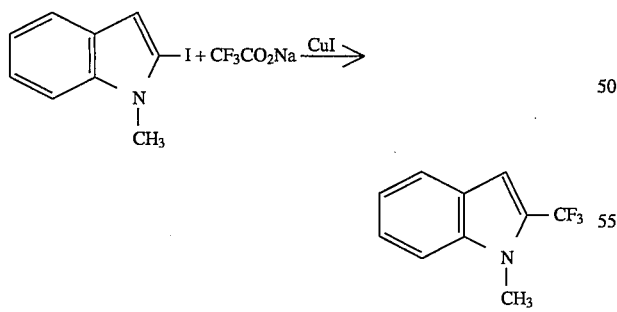

A mixture of 1-methyl-2-iodoindole (4.40 g, 17.3 mmole), sodium trifluoroacetate (24.0 g, 176.5 mmole) and copper(I)iodide (17.1 g, 89.8 mmole)in N-methylpyrrolidone is heated at 160° C. for 6 hours, cooled to room temperature, diluted with water and filtered through diatomaceous earth to remove copper salts. The filtrate is extracted with ether. The extracts are combined, washed with water, dried over $MgSO_4$ and concentrated in vacuo to give a residue. The residue is chromatographed using silica gel and 4:1 hexanes:ethyl acetate as eluent to give the title product as a pale yellow oil which crystallized on standing, 119 g (37% yield), mp 28°–32° C., identified by IR, $^1HNMR$ and $^{19}FNMR$ analyses.

EXAMPLE 3

Preparation of 5-Chloro-2-iodo-1-methylindole

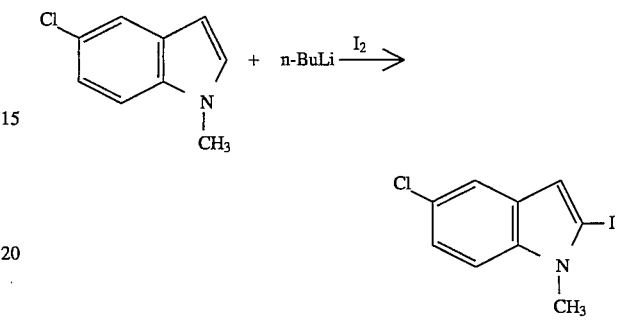

A mixture of 5-chloro-1-methylindole (10.0 g, 60.4 mmole) and n-butyl lithium (29 mL of 2.5M sol'n in hexanes, 72.5 mmole) in diethyl ether is heated at reflux temperature for 3 hours, cooled to 0° C., treated with iodine (18.4 g, 72.5 mmole), stirred at 0° C. for 1 hour, warmed to room temperature, stirred for 1 hour, and treated with aqueous sodium sulfite. After phase separation, the organic phase is dried over $MgSO_4$ and concentrated in vacuo to give the title product as a brown oil which solidified on standing, 16.5 g (93.7% yield). The title product is used as in Example 4.

EXAMPLE 4

Preparation of 5-Chloro-1methyl-2-(trifluoromethyl)indole

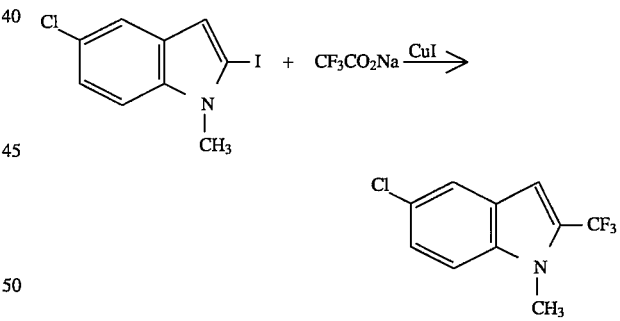

A mixture of 5-chloro-2-iodo-1-methylindole obtained from Example 3 (16.5 g, 56.6 mmole), sodium trifluoroacetate (76.2 g, 56.0 mmole) and copper (I) iodide (10.6 g, 56.0 mmole) in N-methylpyrrolidone is heated at 160° C. for about 8 hours, cooled to room temperature, diluted with water and filtered through diatomaceous earth. The filtrate is extracted with diethyl ether. The extracts are combined, washed with water, dried over $MgSO_4$ and concentrated in vacuo to give a black oil residue. The residue is chromatographed using silica gel and 15:1 hexanes:ethyl acetate to give a yellow oil. The oil is chromatographed a second time using the same eluent and silica gel to give the title product as a yellow oil, 2.92 g (22% overall yield from 5-chloro-1-methylindole), identified by IR, $^1HNMR$, $^{13}CNMR$ and $^{19}FNMR$ analyses.

EXAMPLE 5

Preparation of 5-Chloro-3-cyano-1-methyl-2-(trifluoromethyl)indole

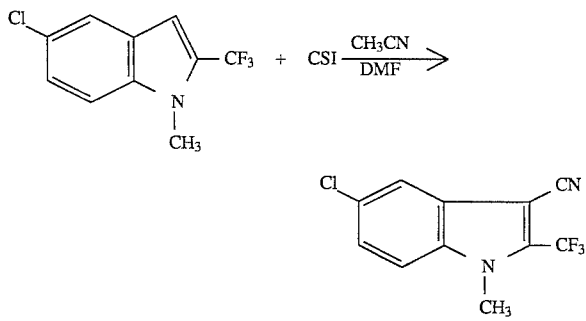

A solution of 5-chloro-1-methyl-2-(trifluoromethyl)indole (1.79 g, 7.7 mmole) in acetonitrile is cooled to 0° C., treated with chlorosulfonylisocyanate (CSI) (1.0 mL 11.5 mmole) stirred until starting indole cannot be observed by thin layer chromatography, treated with 5 mL of dimethylformamide (DMF), stirred for 0.5 hour and diluted with diethyl ether and water. The phases are separated. The organic phase is washed with water, dried over $Na_2SO_4$ and concentrated in vacuo. The resultant residue is chromatographed using silica gel and 4:1 hexanes:ethyl acetate as eluent to give the title product as a white solid, 0.99 g (49.7% yield) mp 166°–167.5° C., identified by IR, $^1$HNMR, $^{13}$CNMR, $^{19}$FNMR and mass spectral analyses.

EXAMPLE 6

Preparation of 6-Chloroindole

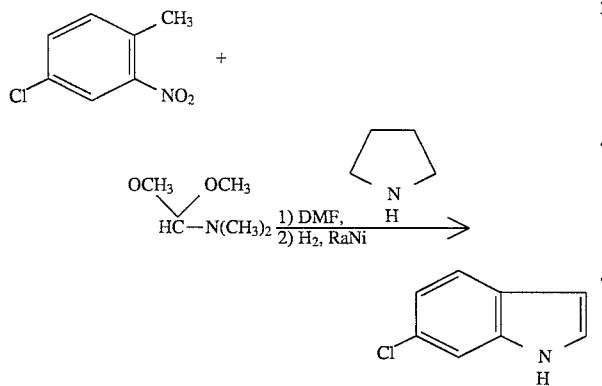

A mixture of 4-chloro-2-nitrotoluene (34 g, 0.2 mole), dimethylformamide dimethyl acetal (28 mL, 0.2 mole) and pyrrolidine (25 mL 0.3 mole) in dimethylformamide (DMF) is heated at 100° C. for 72 h, cooled to room temperature and concentrated in vacuo to give a deep red residue. The residue is taken up in methanol/tetrahydro-furan (1:1), treated with about 2 mL of a Raney nickel slurry and hydrogenated at atmospheric pressure. The reaction is monitored by GC, TLC and $H_2$ uptake. After 2 hours, the hydrogenation is continued at 20 psi–40 psi for a total hydrogenation time of 24 hours. The resultant reaction mixture is filtered through diatomaceous earth. The filtercake is washed with methylene chloride and the combined filtrate is washed sequentially with 1N HCl and saturated $NaHCO_3$, dried over $MgSO_4$ and concentrated in vacuo to give a brown oil residue. The residue is crystallized in hexanes to give the title product as a brown solid, 22 g (72.6% yield), identified by IR, $^1$HNMR, $^{13}$CNMR and mass spectral analyses.

EXAMPLE 7

Preparation of 6-Chloro-1-methylindole

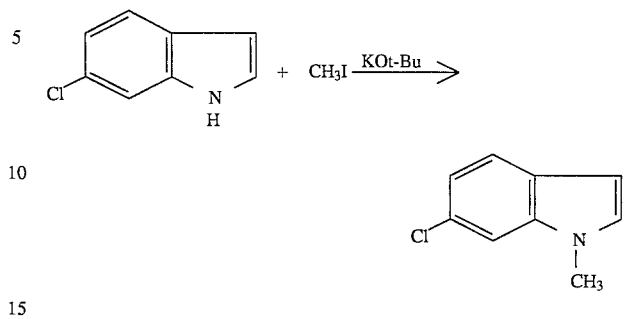

A mixture of 6-chloroindole (22.0 g, 0.145 mole) and potassium t-butoxide (KOt-Bu) (20.0 g 0.179 mole) in tetrahydrofuran at room temperature is treated dropwise with methyl iodide (11.2 mL, 0.179 mole), allowed to stir at ambient temperatures for about 1 hour and diluted with a mixture of pet ether and water. The phases are separated. The organic phase is washed with 1N HCL and water, dried over $Na_2SO_4$ and concentrated to a brown oil. After chromatography (silica gel/4:1 hexanes:ethyl acetate), the oil is distilled to afford the title product as a colorless oil, 16.25 g (67% yield), bp 110°–115° C./4 mm Hg, identified by IR, $^1$HNMR, $^{13}$CNMR, mass spectral and microanalyses.

EXAMPLE 8

Preparation of 6-Chloro-2-iodo-1-methylindole

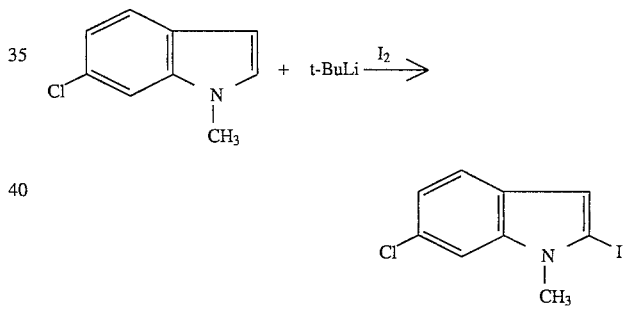

A solution of 6-chloro-1-methylindole (0.83 g, 5.0 mmole) in diethyl ether is treated with 1.7M t-butyl lithium in hexanes (3.5 mL, 6.0 mmole) at 0° C., stirred at ambient temperatures for 0.25 hour, treated with $I_2$ (1.52 g, 6.0 mmole), stirred at room temperature until reaction is complete by TLC analysis, treated with aqueous sodium sulfite and extracted with diethyl ether. The combined ether extracts are dried over $MgSO_4$ and concentrated in vacuo to afford the title product as a brown solid, 1.52 g (contains ether). The product is used as is in Example 9.

EXAMPLE 9

Preparation of 6-Chloro-1-methyl-2-(trifluoromethyl)indole

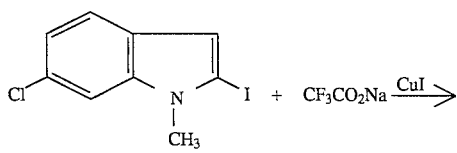

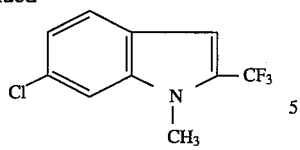

A mixture of 6-chloro-2-iodo-1-methylindole, obtained in Example 8, (1.5 g (96.7% purity), 5.0 mmole), sodium trifluoroacetate (6.8 g, 50 mmole) and copper (I) iodide (0.95 g, 5.0 mmole) in N-methylpyrrolidone is heated at about 160° for 2 hours and 190° C. for 1 hour, cooled to room temperature, diluted with water and filtered through diatomaceous earth. The filtrate is extracted with diethyl ether. The combined extracts are washed with water, dried over $MgSO_4$ and concentrated in vacuo to give a residue. The residue is chromatographed (silica gel/4:1 hexanes-:ethyl acetate) to afford the title product as a yellowish crystalline solid 0.51 g (46% yield), mp 75°–78° C., identified by IR, $^1HNMR$, $^{13}CNMR$, $^{19}FNMR$, mass spectral and microanalyses.

EXAMPLE 10

Preparation of 6-Chloro-1-methyl-2-(trifluoromethyl)indole-3-carbonitrile

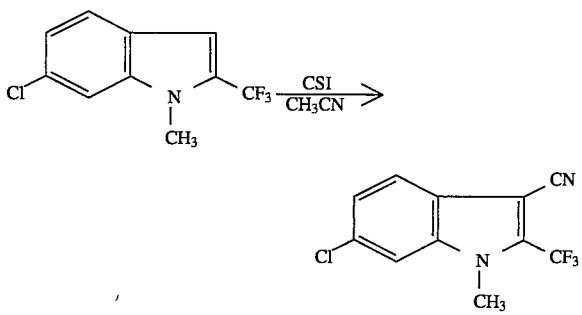

Using essentially the same procedure described in Example 5, the title product is obtained as a white solid in 80.4% yield after chromatography, mp 142.5°–145° C., identified by IR, $^1HNMR$, $^{13}CNMR$, $^{19}FNMR$ and mass spectral analyses.

EXAMPLE 11

Preparation of 6-Chloro-1-(ethoxymethyl)-2-(trifluoromethyl)indole-3-carbonitrile

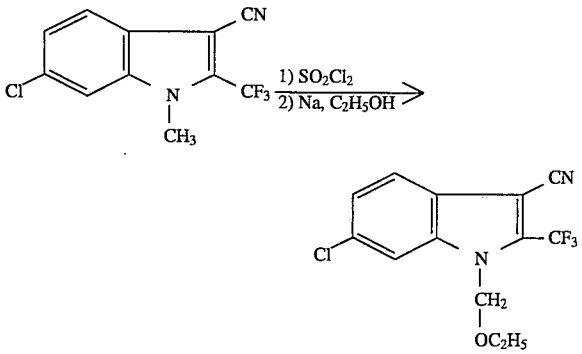

A mixture of 6-chloro-3-cyano-1-methyl-2-(trifluoromethyl)indole (1.08 g, 4.2 mmole) and thionyl chloride (0.68 mL, 8.4 mmole) in carbon tetrachloride is heated at reflux temperature for 18 hours, cooled to room temperature and concentrated in vacuo for 18 hours to remove all volatiles. The residue is dissolved in ethanol and treated with a solution of sodium metal (0.38 g, 16 mmole) in ethanol, stirred or 0.5 hour at room temperature and diluted with diethyl ether. The diluted reaction mixture is washed with water, dried over $Na_2SO_4$ and concentrated in vacuo to give a residue. The residue is chromatographed (silica gel/4:1 hexanes: ethyl acetate) to afford the title product as an off-white solid, 0.66 g (52% yield) mp 83°–86° C., identified by IR, $^1HNMR$, $^{13}CNMR$, $^{19}FNMR$ and mass spectral analyses.

EXAMPLE 12

Preparation of 6-Chloro-3-nitro-1-methyl-2-(trifluoromethyl)indole

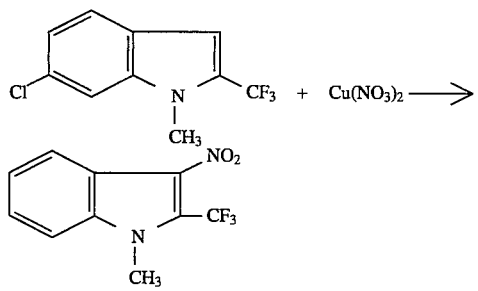

A solution of 6-chloro-1-methyl-2-(trifluoromethyl)indole (1.16 g, 5.0 mmole ) in acetic anhydride is treated with $Cu(NO_3)_2 \cdot 3H_2O$ (1.20 g, 5.0 mmole) stirred at 0°–25° C. for 3 hours, and partitioned between water and diethyl ether. The organic phase is washed with water and saturated $NaHCO_3$, dried over $Na_2SO_4$ and concentrated in vacuo to give a residue. The residue is chromatographed (silica gel/4:1 hexanes: ethyl acetate) to afford the title product as white leaflets, 0.87 g (62.41% yield), mp 157°–159.9° C., identified by IR, $^1HNMR$, $^{13}CNMR$, $^{19}FNMR$ and mass spectral analyses.

EXAMPLE 13

Preparation of 5-Bromo-2-(trifluoromethyl)indole-3-carbonitrile

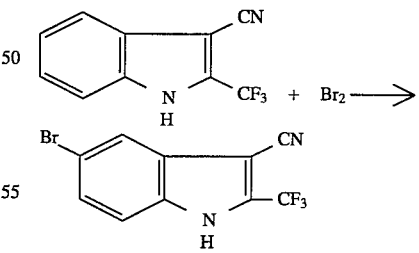

A solution of 3-cyano-2-(trifluoromethyl)indole (1.05 g, 5.0 mmole) in acetic acid is treated with $Br_2$ (0.6 mL, 6.0 mmole) at room temperature, and stirred until reaction is complete by TLC. The reaction mixture is worked up as described in Example 22 to afford the title product as a white solid after chromatography (silica gel and 4:1 hexanes:ethyl acetate) and crystallization, 0.95 g (65% yield), mp 188°–191.5° C., identified by IR, $^1HNMR$, $^{19}FNMR$ and mass spectral analyses.

EXAMPLE 14

Preparation of 5,6- and 6,7-Dichloro-3-cyano-1-methyl-2-(trifluoromethyl)indole

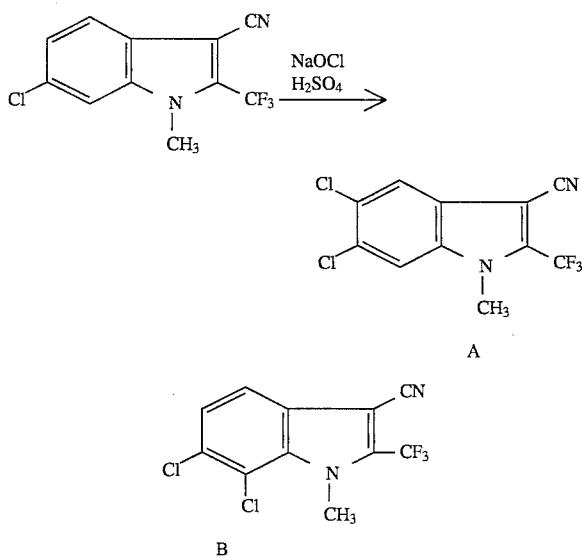

A suspension of 6-chloro-3-cyano-2-(trifluoromethyl)indole (0.51 g, 2.0 mmole) in 2 mL H₂SO₄ and 6 mL water is treated with acetic acid to achieve dissolution; the solution is treated with incremental portions of NaOCl (2.8 mL, 2.0 mmole) and H₂SO₄ until reaction is complete (a total of 4 portions, 8.0 mmole NaOCl). The resultant reaction mixture is poured into water and extracted with diethyl ether. The organic phase is washed with NaHCO₃ until neutralized, dried over MgSO₄ and concentrated in vacuo to give a residue containing the title product mixture. The mixture is separated by column chromatography (silica gel/4:1 hexanes: ethyl acetate) to afford:

A—5,6 dichloro-3-cyano-1-methyl-2-(trifluoromethyl)indole as a white solid, 0.077 g (13% yield), mp 175°–180° C., identified by IR, ¹HNMR, ¹⁹FNMR and mass spectral analyses, and B—6,7-dichloro-3-cyano-1-methyl-2-(trifluoromethyl)indole as a white solid, 0.082 g (14% yield), mp 220°–223° C., identified by IR, ¹HNMR, ¹⁹FNMR and mass spectral analyses.

EXAMPLE 15

Preparation of 5,6-Dichloro-2-(trifluoromethyl)indole and 5,6-dichloro-1-ethoxy-2-(trifluoromethyl)indole

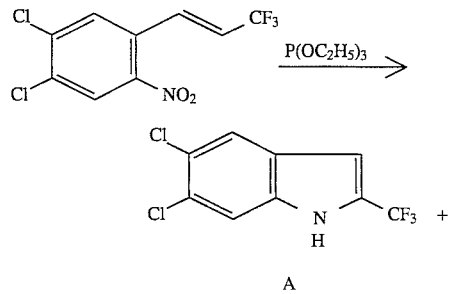

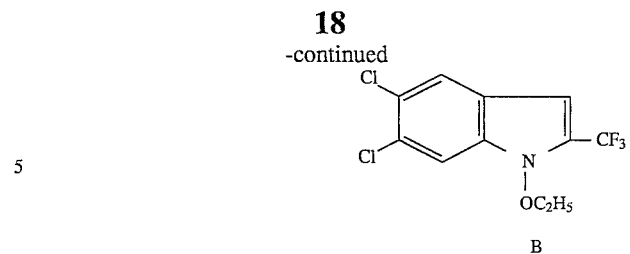

A mixture of 4,5-dichloro-2-nitro-β-trifluoromethyl styrene (5.5 g, 19.2 mmole) and triethylphosphite (26 mL, 153 mmole) is heated at 160° C. for 4.5 hours (monitored by GC, TLC and NMR), cooled to room temperature, concentrated in vacuo to give a residue. The residue is taken up in ether, washed sequentially with water and brine, dried over MgSO₄ and concentrated in vacuo to afford the title product mixture. The mixture is separated chromatographically (silica gel/10:1 hexanes:ethyl acetate) to afford:

A—5,6 dichloro-2-(trifluoromethyl)indole as colorless leaflets 0.82 g (17% yield)mp 96°–98° C., identified by IR, ¹HNMR, ¹³CNMR, ¹⁹FNMR and mass spectral analyses, and B—5,6-dichloro-1-ethoxy-2-(trifluoromethyl)-indole as a yellow solid, 1.19 g (20.7% yield, mp 71°–73.5° C., identified by IR, ¹HNMR, ¹⁹FNMR and mass spectral analyses.

EXAMPLE 16

Preparation of 6,7-Dichloro-1-(ethoxymethyl)-2-(trifuloromethyl)indole-3-carbonitrile

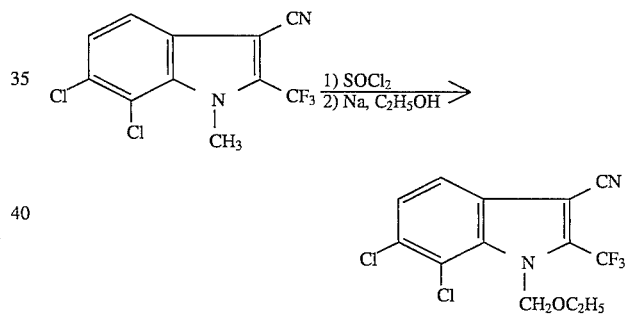

Using essentially the same procedure described in Example 11 the title product is obtained in 44% yield after chromatography (silica gel/4:1 hexanes:ethyl acetate) as a white solid, mp 122°–127° C., identified by IR, ¹HNMR, ¹⁹FNMR and mass spectral analyses.

EXAMPLE 17

Preparation of 5,6-Dichloro-2-(trifluoromethyl)indole-3-carbonitrile

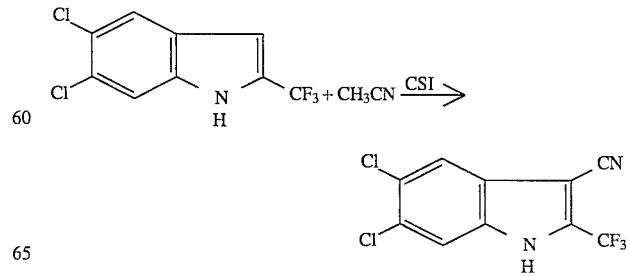

Using essentially the same procedure described in Example 5, the title product is obtained in 19.6% yield after chromatography (silica gel/8:1 hexanes:ethyl acetate) as a white solid, mp >260° C., identified by IR, $^1$HNMR, $^{19}$FNMR and mass spectral analyses.

EXAMPLE 18

Preparation of 5-Nitro-2-(trifluoromethyl)indole

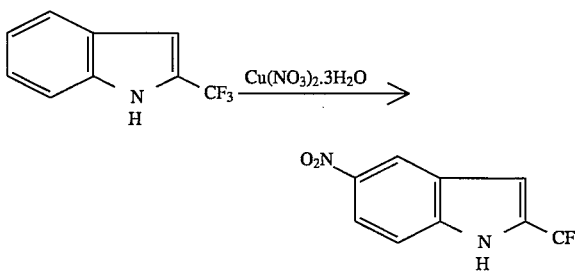

A solution of 2-(trifluoromethyl)indole (0.2 g, 1.1 mmole) in acetic anhydride is treated with (0.131 g, 0.54 mmole of) Cu(NO$_3$)$_2$.3H$_2$O at 0° C., stirred for 2.5 hours at room temperature and diluted with water and ether. The phases are separated; the organic phase is washed sequentially with saturated NaHCO$_3$ and brine, dried over MgSO$_4$ and concentrated in vacuo to give a yellow solid residue. The residue is chromatographed (silica gel/20% ethyl acetate in hexanes) to give the title product as a yellow solid, 0.073 g (29.4% yield), mp 190°–193° C., identified by IR, $^1$HNMR, $^{19}$FNMR and mass spectral analyses.

EXAMPLE 19

Preparation of 5-Nitro-2-(trifluoromethyl)indole and 3-cyano-6-nitro-2-(trifluoromethyl)indole-3-carbonitrile

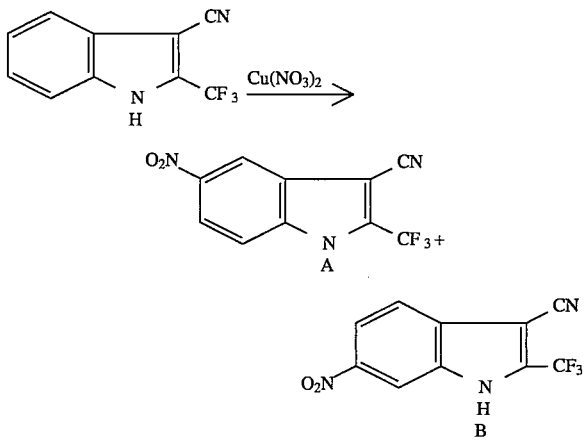

Using essentially the same procedure described in Example 18 and substituting 3-cyano-2-(trifluoromethyl)indole as substrate the title product mixture is obtained. The mixture is separated chromatographically (silica gel/20% ethyl acetate in hexanes) and recrystallized from ethyl acetate/hexanes to give:

A—3-cyano-5-nitro-2-(trifluoromethyl)indole as beige crystals in 41% yield, mp>260° C. identified by IR, $^1$HNMR, $^{19}$FNMR and mass spectral analyses, and B—3-cyano-6-nitro-2-(trifluoromethyl)indole as a beige solid in 6% yield, mp>230° C., identified by IR, $^1$HNMR, $^{19}$FNMR and mass spectral analyses.

EXAMPLE 20

Preparation of 3,5-Dinitro-2-(trifluoromethyl)indole

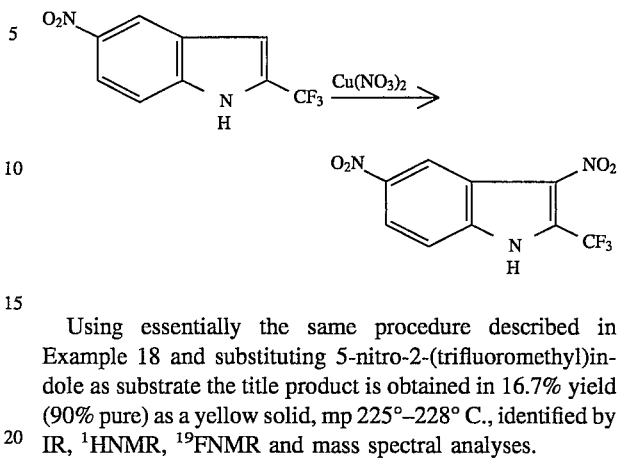

Using essentially the same procedure described in Example 18 and substituting 5-nitro-2-(trifluoromethyl)indole as substrate the title product is obtained in 16.7% yield (90% pure) as a yellow solid, mp 225°–228° C., identified by IR, $^1$HNMR, $^{19}$FNMR and mass spectral analyses.

EXAMPLE 21

Preparation of 5,6- and 5,7-Dinitro-2-(trifluoromethyl)indole-3-carbonitrile

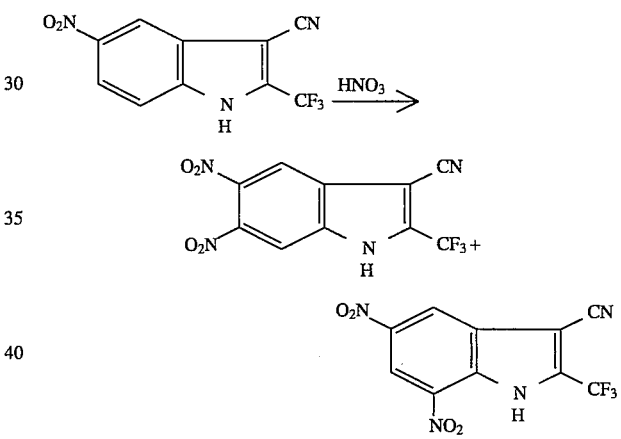

A mixture of 3-cyano-5-nitro-2-(trifluoromethyl)indole (0.23 g, 0.90 mmole) in 7 mL of fuming nitric acid (90%), under nitrogen, is stirred at 0° C. for 0.5 hour, stirred for 19 hours at room temperature, poured into ice water and extracted with ethyl acetate. The combined extracts are washed sequentially with saturated NaHCO$_3$ and brine, dried over MgSO$_4$ and concentrated in vacuo to give a brown solid residue. After chromatography and crystallization, the title product mixture is obtained as a yellow solid, 0.104 g (3.7% yield), mp >230° C., identified by IR, $^1$HNMR and $^{19}$FNMR analyses.

EXAMPLE 22

Preparation of 5-Methoxy-2-(trifluoromethyl)indole

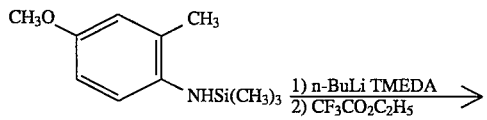

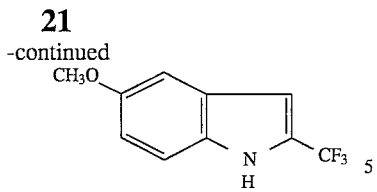

Tetramethylethylenediamine (TMEDA) (49 g, 0.42 mole), under nitrogen, is treated with n-butyl lithium (168 mL of 2.57N in hexanes, 0.42 mole) at 0° C., stirred for 0.5 hour at room temperature, treated dropwise with N-(trimethylsilyl)-4-methoxy-o-toluidine (40.0 g, 0.19 mole), heated at reflux temperature for 4 hours, cooled to −78° C., diluted with dry cyclohexane, treated dropwise with ethyl trifluoroacetate (45 g, 0.23 mole), stirred at −78° C. for 0.5 hour, warmed to room temperature and quenched with saturated NH$_4$Cl solution. The mixture is extracted with diethyl ether. The combined extracts are washed sequentially with saturated NH$_4$Cl and brine, dried over Na$_2$SO$_4$ and concentrated in vacuo to give a brown oil residue. The oil is chromatographed (silica gel/10% ethyl acetate in hexanes) to give the title product as white needles, 5.0 g (12% yield), mp 60° C. (after recrystallization from pentane), identified by IR, $^1$HNMR, $^{13}$CNMR, $^{19}$FNMR and mass spectral analyses.

EXAMPLE 23

Preparation of 3-cyano-5-methoxy-2-(trifluoromethyl)indole

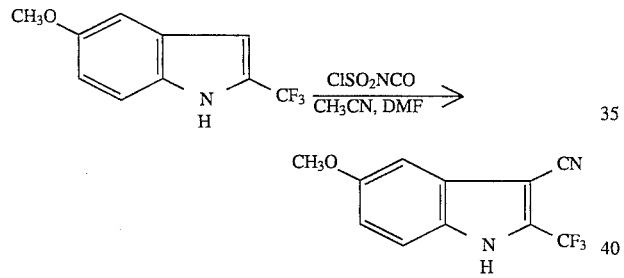

A solution of 5-methoxy-2-(trifluoromethyl)indole (3.0 g, 13.0 mmole) in acetonitrile is treated dropwise with chlorosulfonyl isocyanate (2.02 g, 14.3 mmole) at 0° C., stirred at ambient temperatures for 2.5 hours, treated with dimethylformamide (DMF) (2.1 g, 28.6 mmole), stirred at ambient temperatures for 0.75 hour and poured into water. The resultant mixture is extracted with diethyl ether. The combined extracts are washed sequentially with water and brine, dried over MgSO$_4$ and concentrate in vacuo to give a brown oil residue. The oil is crystallized in ether/hexanes to give the title product as brown crystals, 0.78 g (25% yield), mp 189°–190° C., identified by IR, $^1$HNMR, $^{13}$CNMR and $^{19}$FNMR.

EXAMPLE 24

Preparation of 5,6-Dichloro-2-[(2-chloro-1,1,2-trifluoroethyl)thio]indole

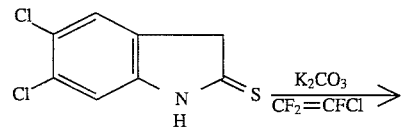

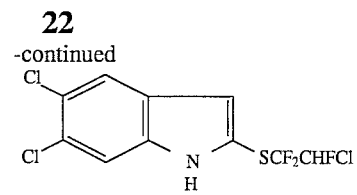

A mixture of 5,6-dichloroindolene-2-thione (3.71 g, 17.0 mmole) and potassium carbonate (2.35 g, 17.0 mmole) in isopropanol is placed in a pressure tube, treated with chlorotrifluoroethylene (2.18 g, 18.7 mmole), sealed and stirred for 16 hours at room temperature. After the seal is broken, the reaction mixture is concentrated in vacuo, diluted with ethyl acetate, washed sequentially with water and brine, dried over MgSO$_4$ and reconcentrated in vacuo to afford a dark residue. Flash column chromatography (silica gel/1:10 ethyl acetate: hexanes) gives the title product as an off-white solid, 3.4 g (56% yield) mp 54°–60° C., identified by IR, $^1$HNMR and $^{19}$FNMR analyses.

EXAMPLES 25–27

Preparation of Substituted 2-thioindole compounds

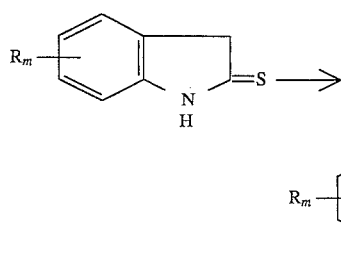

Using essentially the same procedure described in Example 24 and substituting the appropriate indoline-2-thione substrate and desired olefin, the following compounds shown in Table I are obtained.

TABLE I

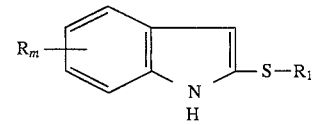

| Example Number | R$_m$ | R$_1$ | % Yield | mp °C. |
|---|---|---|---|---|
| 25 | H | CF$_2$CHF$_2$ | 33 | oil |
| 26 | H | CF$_2$CHFCl | 54 | oil |
| 27 | 5-Br | CF$_2$CHFCl | 49 | oil |

EXAMPLE 28

Preparation of 2-[(2-chloro-1,1,2-trifluoroethyl)thio]indole-3-carbonitrile

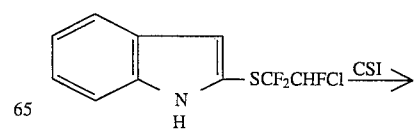

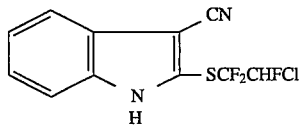

A solution of 2-[(2-chloro-1,1,2-trifluoroethyl)thio]indole (0.64 g, 2.4 mmole) in acetonitrile is treated with a solution of chlorosulfonylisocyanate (CSI) (0.85 g, 6.0 mmole) in acetonitrile at ice bath temperatures, stirred at room temperature for 3 hours, treated with dimethylformamide (0.88 g, 12 mmole) at 0° C., stirred for 1 hour at ambient temperatures, poured into ice water and extracted with ethyl acetate. The combined extracts are washed with brine, dried over MgSO$_4$ and concentrated in vacuo to give a residue. Flash chromatography (silica gel/1:4 ethyl acetate:hexanes) affords the title product as a white solid, 0.44 g (63% yield), mp 134°–136° C., identified by IR, $^1$HNMR and $^{13}$CNMR.

EXAMPLE 29

Preparation of 5-Bromo-2[(2-chloro-1,1,2-trifluoroethyl)thio]indole-3-carbonitrile

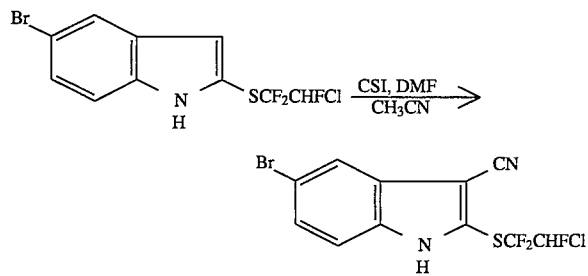

Using essentially the same procedure described in Example 28 but employing 5-bromo-2[(2-chloro-1,1,2-trifluoroethyl)thio]indole, the title product is obtained as a white solid, mp 187°–192° C., identified by IR, $^1$HNMR and $^{13}$CNMR.

EXAMPLE 30 preparation of 2-(trifluoromethyl)-3-[(trifluoromethyl)thio]indole

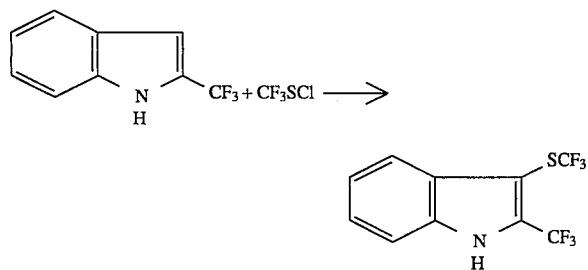

A mixture of 2-(trifluoromethyl)indole (1.85 g, 0.01 mole) and 3 drops of triflic acid in dichloroethane is heated at 65° C. in a sealed pressure tube for 72 hours, cooled, concentrated in vacuo, diluted with ethyl acetate, washed sequentially with saturated NaHCO$_3$ and brine, dried over NaSO$_4$ and reconcentrated in vacuo to give a residue. Flash column chromatography (silica gel/1:10 ethyl acetate:hexanes) affords the title product as a yellow oil, 2.03 g (71% yield), identified by IR, $^1$HNMR, $^{13}$CNMR, $^{19}$FNMR and mass spectral analyses.

EXAMPLE 31

Preparation of 2,6-Dibromo-3-[(trifluoromethyl)thio]indole

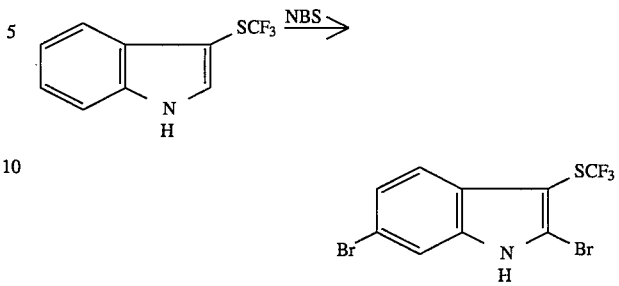

A mixture of 3-[(trifluoromethyl)thio]indole (0.776 g, 3.57 mmole), 1.0 g of silica gel and N-bromosuccinimide (NBS) (1.27 g, 71.9 mmole) in methylene chloride is stirred at room temperature for 2 hours and concentrated in vacuo to give a residue. Flash column chromatography (silica gel/15:85 ethyl acetate:hexanes) of the residue affords the title product as a brown syrup, 0.41 g (30.6% yield), identified by IR, $^1$HNMR, $^{13}$CNMR, $^{19}$FNMR and mass spectral analyses.

EXAMPLE 32

Preparation of 5-Bromo-2[(2-chloro-1,1,2-trifluoroethyl)thio]indole-3-carbonitrile

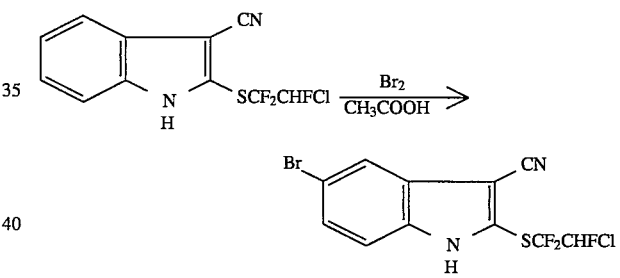

A solution of 2[(2-chloro-1,1,2-trifluoroethyl)thio]indole (0.75 g, 2.58 mmole) in acetic acid is treated with bromine (0.45 g, 2.84 mmole), stirred for 16 hours at room temperature, poured into water and filtered. The white solid filtercake is dissolved in ethyl acetate, washed with brine, dried over MgSO$_4$ and concentrated in vacuo to give a residue. The residue is chromatographed (silica gel/1:4 ethyl acetate:hexanes) to afford the title product as a white solid, 0.28 g (29% yield), mp 187°–192° C., identified by IR, $^1$HNMR, $^{13}$CNMR, $^{19}$FNMR and mass spectral analyses.

EXAMPLES 33–36

Preparation of Bromo- and Dibromo-substituted -3-[(trifluoromethyl)indole compounds

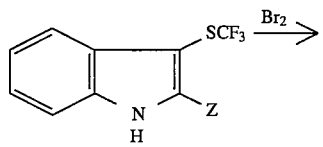

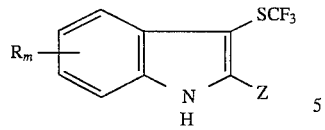

Using essentially the same procedure described in Example 32, substituting the appropriately substituted indole substrate and employing one or two equivalents of Br$_2$, the following compounds shown in Table III are obtained.

TABLE III

| Example Number | R$_m$ | Z | mp °C. |
|---|---|---|---|
| 33 | 5-Br | CF$_3$ | 76–78 |
| 34 | 5,6-diBr | CF$_3$ | syrup |
| 35 | 5-Br | CN | 172–175 |
| 36 | 6-Br | CN | 153–156 |

EXAMPLE 37

Preparation of 2-(Trifluoromethyl)-3-[(trifluoromethyl)sulfinyl]indole

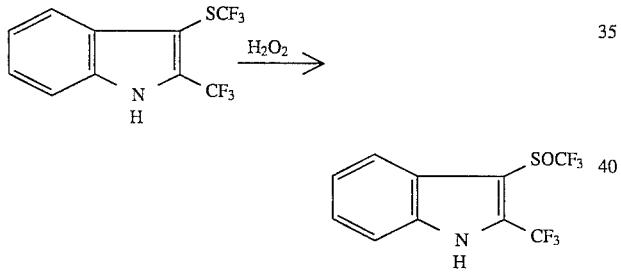

A mixture of 2-(trifluoromethyl)-3-[(trifluoromethyl)thio]indole (0.96 g, 3.36 mmole) and 30% hydrogen peroxide (1.15 mL, 10.1 mmole) in acetic acid is heated at 50° C. for 16 hours, cooled to room temperature, poured onto water and filtered. The filter cake is air-dried to give the title product as a colorless solid, 0.535 g (50% yield), mp 183°–185° C., identified by IR, $^1$HNMR, $^{13}$CNMR, $^{19}$FNMR and mass spectral analyses.

EXAMPLES 38–41

Preparation of Substituted-3-[(haloalkyl)sulfinyl]indole compounds

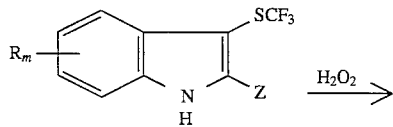

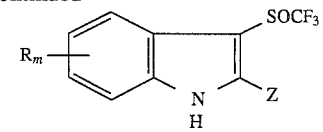

Using essentially the same procedure described in Example 37 and employing the appropriate 3-[(trifluoromethyl)thio]indole substrate, the compounds shown in Table IV are obtained.

TABLE IV

| Example Number | Rm | Z | mp °C. |
|---|---|---|---|
| 38 | 5-Br | CF$_3$ | 210–212 |
| 39 | H | CN | 154–156 |
| 40 | H | CONH$_2$ | 185 (decompose) |
| 41 | 6-Br | Br | 95–97 |

EXAMPLE 42

Preparation of 2[(2-Chloro-1,1,2-trifluoroethyl)sulfonyl]indole-3-carbonitrile

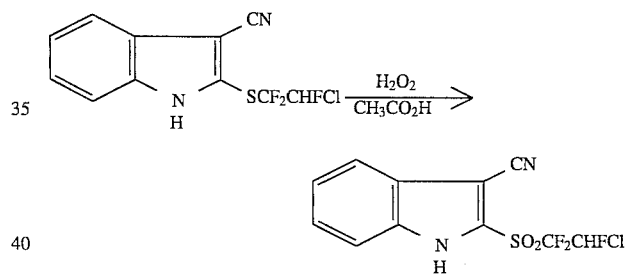

A mixture of 2[(2-chloro-1,1,2-trifluoroethyl)thio]indole-3-carbonitrile (2.39 g 8.22 mmole) and 30% hydrogen peroxide (2.80 g, 24.7 mmole) in acetic acid is heated at 60° C. for 16 hours, cooled to room temperature poured onto water and filtered. The filtercake is air-dried to afford the title product as a white solid, 2.37 g (89% yield), mp 164°–167° C., identified by IR, $^1$HNMR, $^{13}$CNMR and $^{19}$FNMR analyses.

EXAMPLES 43–48

Preparation of Substituted-sulfonylindole compounds

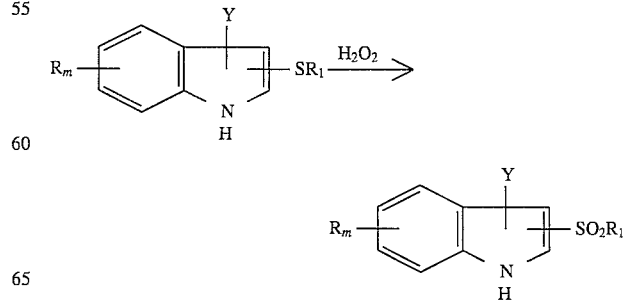

Using essentially the same procedure described in Example 42, employing the appropriate thioindole substrate and heating to about 60°–90° C., the compounds shown in Table V are obtained.

TABLE V

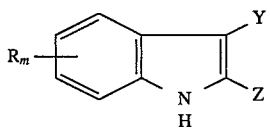

| Example Number | $R_m$ | Z | Y | mp °C. |
|---|---|---|---|---|
| 43 | 5,6-diCl | $SO_2CF_2CHFCl$ | CN | 178–180 |
| 44 | 5-Br | $SO_2CF_2CHFCl$ | CN | 220–223 |
| 45 | H | H | $SO_2CF_3$ | 115–118 |
| 46 | H | $CF_3$ | $SO_2CF_3$ | 104–107 |
| 47 | H | CN | $SO_2CF_3$ | 152–154 |
| 48 | 5-Br | CN | $SO_2CF_3$ | >230 |

EXAMPLE 49

Preparation of 3-Bromo-5,6-dichloro-2[(2-chloro-1,1,2-trifluoroethyl)sulfonyl]indole

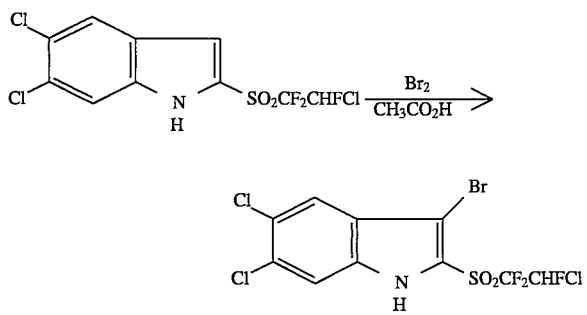

A mixture of 5,6-dichloro-2[(2-chloro-1,1,2-trifluoroethyl)sulfonyl]indole (0.84 g, 2.29 mmole) and sodium acetate (0.21 g, 2.52 mmole in acetic acid is treated with bromine (0.40 g, 2.52 mmole), stirred for 0.5 hour at room temperature, poured onto water and filtered. The filtercake is air-dried to afford the title product as a white solid, 0.93 g (91% yield), mp 200°–205° C., identified by IR, $^1$HNMR and $^{19}$FNMR spectral analyses.

EXAMPLE 50

Preparation of 2-[(2-chloro-1,1,2-trifluoroethyl)sulfonyl]-1-(ethoxymethyl)indole-3-carbonitrile

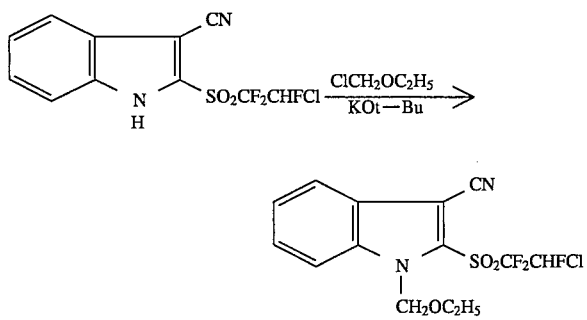

A mixture of 2[(2-chloro-1,1,2-trifluoroethyl)sulfonyl]indole-3-carbonitrile (1.0 g, 3.1 mmole), chloromethylethylether (0.35 g, 3.72 mmole), and 95% potassium t-butoxide (0.44 g, 3.72 mmole) in tetrahydrofuran is stirred at room temperature for 16 hours, treated with 1.55 mmole additional chloromethylethylether and potassium t-butoxide, stirred at room temperature for another 16 hours, concentrated in vacuo, diluted with ethyl acetate, washed sequentially with water and brine, dried over $MgSO_4$ and reconcentrated in vacuo to give an oil residue. After flash column chromatography (silica gel/1:4 ethyl acetate: hexanes) the title product is obtained as a white solid, 0.32 g (28% yield), mp 97°–100° C., identified by IR and $^1$HNMR analyses.

EXAMPLES 51–61

Preparation of Substituted-1-(ethoxymethyl)indole compounds

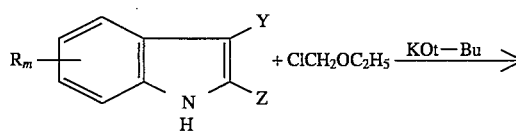

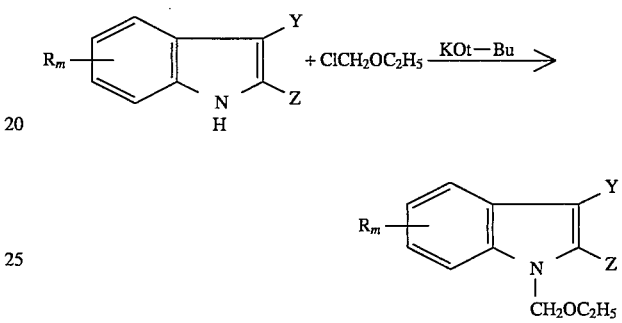

Using essentially the same procedure described in Example 50 and employing the appropriately substituted indole, the compounds in Table VI are obtained.

TABLE VI

| Example Number | $R_m$ | Z | Y | mp °C. |
|---|---|---|---|---|
| 51 | 5-Br | $SO_2CF_2CHFCl$ | CN | 146–147 |
| 52 | H | $CF_3$ | $SOCF_3$ | 99–102 |
| 53 | H | H | $SO_2CF_3$ | 97–98 |
| 54 | H | $CF_3$ | $SCF_3$ | 58–60 |
| 55 | H | H | $SCF_3$ | 60–62 |
| 56 | 5-Br | $CF_3$ | $SCF_3$ | oil |
| 57 | H | CN | H | 50–52 |
| 58 | H | CN | $SOCF_3$ | 101–103 |
| 59 | H | CN | $SO_2CF_3$ | 124–126 |
| 60 | H | $CF_3$ | $SO_2CF_3$ | 93–94 |
| 61 | 6-Br | Br | $SCF_3$ | oil |

EXAMPLE 62

Preparation of 3', 5'-Dichloroacetophenone, (3,5-dichlorophenyl)hydrazone

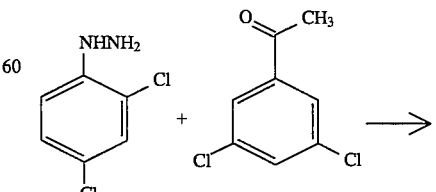

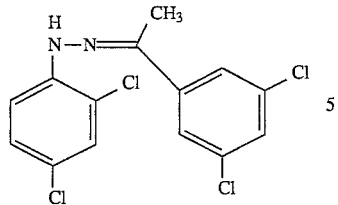

A mixture of 2,4-dichlorophenylhydrazine (4.25 g, 0.025 mole), 3,5-dichloroacetophenone (4.5 g, 0.024 mole) and 1.0 mL HCl in ethanol is heated at reflux temperature for 1 hour, cooled and filtered. The filtercake is air-dried to afford the title product as a white solid, 6.2 g (74% yield), mp 110°–111° C., identified by IR and $^1$HNMR analyses.

EXAMPLE 63

Preparation of 5,7-Dichloro-2-(3,5-dichlorophenyl)indole

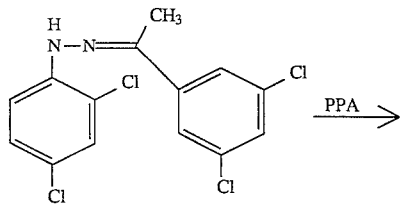

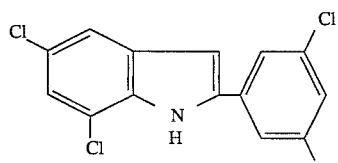

A mixture of 3', 5'-dichloroacetophenone, (3,5-dichlorophenyl)hydrazone (5.2 g, 0.015 mole) and 20 mL of polyphosphoric acid (PPA) is heated at 175°–180° C. for 2 hours, cooled, treated with ice and allowed to stand at room temperature. The resultant mixture is extracted with diethyl ether. The combined extracts are dried over anhydrous $K_2CO_3$ and concentrated in vacuo to afford the title product as a brown solid, 4.35 g (87.8% yield), mp 189°–190° C., identified by IR and $^1$HNMR analyses.

EXAMPLE 64

Preparation of 5,7-Dichloro-2-(3,5-dichlorophenyl)-3-(trifluoromethylcarbonyl)indole

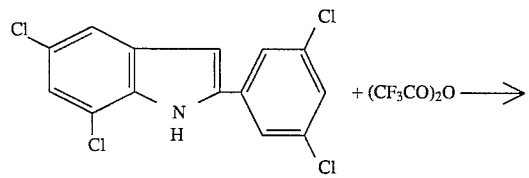

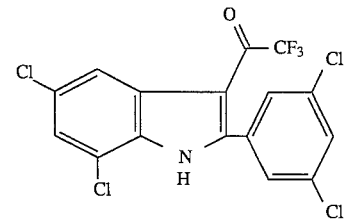

A solution of 5,7-dichloro-2-(3,5-dichlorophenyl)indole (2.0 g, 6.0 mmole) in dimethylformamide is treated with 1.0 mL of trifluoroacetic anhydride at 0°–5° C., stirred for 1 hour, heated at 50°–60° C. for 1 hour, stirred at ambient temperatures for 72 hours, poured over ice and extracted with diethyl ether. The combined extracts are washed sequentially with water and brine, dried over anhydrous $K_2CO_3$ and concentrated in vacuo to afford the title product as an off-white solid, 1.6 g (62% yield), mp 214°–216° C., identified by IR and $^1$HNMR analyses.

EXAMPLE 65

Preparation of 5,7-Dichloro-2-(3,5-dichlorophenyl)-3-nitroindole

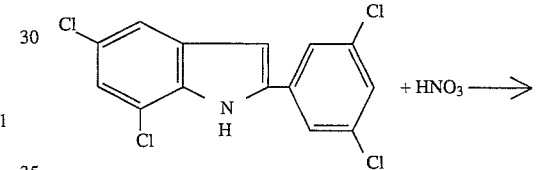

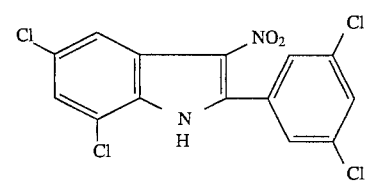

A mixture of 5,7-dichloro-2-(3,5-dichlorophenyl)indole (1.25 g, 3.8 mmole) in acetic acid is treated dropwise with 3 mL of concentrated $HNO_3$ at 90° C., maintained at 90° C. for 1 hour, cooled and filtered. The filtercake is air-dried and recrystallized from methanol/water to afford the title product as a yellow solid, 0.60 g, (42% yield), mp 272°–273° C., identified by IR, $^1$HNMR and elemental analyses.

EXAMPLE 66

Preparation of 5,7-dichloro-2-(3,5-dichlorophenyl)-3-[(trifluoromethyl)sulfonyl]indole

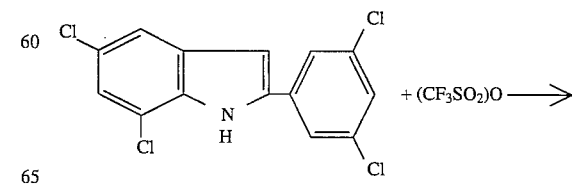

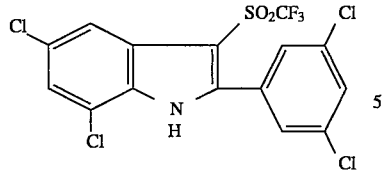

A solution of 5,7-dichloro-2-(3,5-dichlorophenyl)indole (2.0 g, 6.0 mmole) in dimethylformamide is treated with 1 mL of trifluoromethylsulfonyl anhydride at 0°–5° C., stirred at ambient temperatures for 0.5 hour, heated at 50°–60° C. for 1 hour, stirred for 72 hours at room temperature, poured over ice and filtered. The filtercake is air-dried to afford the title product as an off-white solid, 1.65 g (59% yield), mp 300°–302° C., (decompose), identified by IR and $^1$HNMR and elemental analyses.

EXAMPLE 67

Preparation of 3,5,7-trichloro-2-(p-chlorophenyl)indole

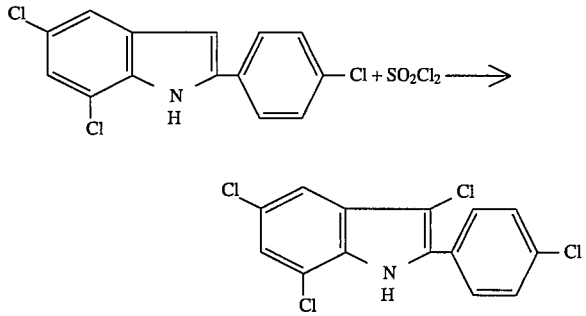

A solution of 5,7-dichloro-2-(p-chlorophenyl)indole in tetrahydrofuran is treated dropwise with 1.0 mL of thionyl chloride, stirred for 16 hours at room temperature, poured over ice and filtered. The filtercake is air-dried to afford the title product as a yellow solid, 0.85 g (76% yield), mp 148°–149° C., identified by IR, $^1$HNMR and elemental analyses.

EXAMPLES 68–85

Preparation of 2-(Substituted phenyl)indole compounds

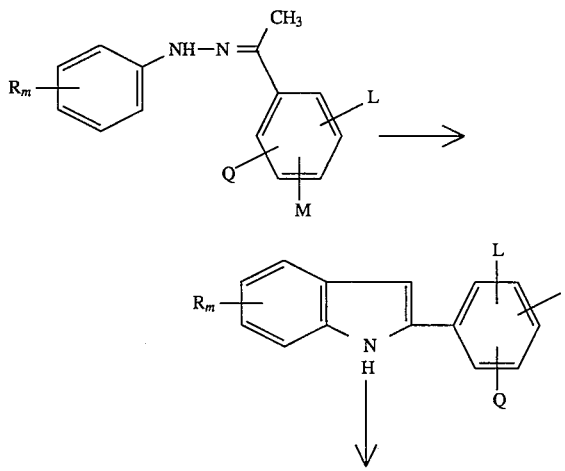

Using essentially the same procedures described in Examples 62 through 67 and employing the appropriate reagents, the compounds shown in Table VII are obtained.

TABLE VII

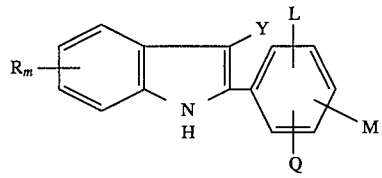

| Example Number | $R_m$ | Y | L | M | Q | mp °C. |
|---|---|---|---|---|---|---|
| 68 | 4,6-diCl | H | 3-Cl | H | 5-Cl | 210–212 |
| 69 | 4,7-diCl | H | 3-Cl | H | 5-Cl | 202–203 |
| 70 | 5,7-diCl | H | H | 4-Cl | H | 165–166 |
| 71 | 4,7-diCl | $NO_2$ | 3-Cl | H | 5-Cl | 115–117 |
| 72 | 4,6-diCl | $NO_2$ | 3-Cl | H | 5-Cl | 258–260 |
| 73 | 4,6-diCl | $NO_2$ | H | 4-Cl | H | 248–250 |
| 74 | 5,7-diCl | $NO_2$ | H | 4-Cl | H | 290–291 |
| 75 | 4,7-diCl | $COCF_3$ | 3-Cl | H | 5-Cl | 198–199 |
| 76 | 4,6-diCl | $COCF_3$ | 3-Cl | H | 5-Cl | 165–166 |
| 77 | 5,7-diCl | $COCF_3$ | H | 4-Cl | H | 112–113 |
| 78 | 4,7-diCl | $SO_2CF_3$ | 3-Cl | H | 5-Cl | 212–213 |
| 79 | 4,6-diCl | $SO_2CF_3$ | 3-Cl | H | 5-Cl | 304–306 |
| 80 | 4,7-diCl | Br | 3-Cl | H | 5-Cl | — |

EXAMPLE 81

Insecticidal And Acaricidal Evaluation Of Test Compounds

Test solutions are prepared by dissolving the test compound in a 35% acetone in water mixture to give a concentration of 10,000 ppm. Subsequent dilutions are made with water as needed.

*Spodoptera eridania*, 3rd instar larvae, southern armyworm (SAW)

A Sieva limabean leaf expanded to 7–8 cm in length is dipped in the test solution wtih agitation for 3 seconds and allowed to dry in a hood. The leaf is then placed in a 100×10 mm petri dish containing a damp filterpaper on the bottom and ten 3rd instar caterpillars. At 5 days, observations are made of mortality, reduced feeding, or any interference with normal molting.

*Diabrotic undecimpunctata howardi*, 3rd instar southern corn rootworm (SCR)

One cc of fine talc is placed in a 30 mL wide-mount screw-top glass jar. One mL of the appropriate acetone suspension is pipetted onto the talc so as to provide 1.25 and 0.25 mg of active ingredient per jar. The jars are set under a gentle air flow until the acetone is evaporated. The dried talc is loosened, 1 cc of millet seed is added to serve as food for the insects and 25 mL of moist soil is added to each jar. The jar is capped and the contents thoroughly mixed on a Vortex Mixer. Following this, ten 3rd instar rootworms are added to each jar and the jars are loosely capped to allow air exchange for the larvae. The treatments are held for 6 days before mortality counts are made. Missing larvae are presumed dead, since they decompose rapidly and cannot be found. The concentrations of active ingredient used in this test correspond approximately to 50 and 10 kg/ha, respectively.

*Tetranychus urticae*(OP-resistant strain), 2-spotted spider mite (TSM)

Sieva limabean plants with primary leaves expanded to 7–8 cm are selected and cut back to one plant per pot. A small piece is cut from an infested leaf taken from the main colony and placed on each leaf of the test plants. This is done about 2 hours before treatment to allow the mites to move over to the test plant to lay eggs. The size of the cut, infested leaf is varied to obtain about 100 mites per leaf. At the time of test treatment, the piece of leaf used to transfer the mites is removed and discarded. The newly mite-infested plants are dipped in the test solution for 3 seconds with agitiation and set in the hood to dry. After 2 days, one leaf is removed and mortality counts are made. After 5 days, another leaf is removed and observations are made of mortality of the eggs and/or newly emerged nymphs.

*Empoasca abrupta*, adults, western potato leafhopper (LH)

A Sieva limabean leaf about 5 cm long is dipped in the test solution for 3 seconds with agitation and placed in a hood to dry. The leaf is placed in a 100×10 mm petri dish containing a moist filter paper on the bottom. About 10 adult leafhoppers are added to each dish and the treatments are kept for 3 days before mortality counts are made.

*Heliothis virenscens*, 3rd instar tobacco budworm (TBW)

Cotton cotyledons are dipped in the test solution and allowed to dry in a hood. When dry, each is cut into quarters and ten sections are placed individually in 30 mL plastic medicine cups containing a 5 to 7 mm long piece of damp dental wick. One 3rd instar caterpillar is added to each cup and a cardboard lid placed on the cup. Treatments are maintained for 3 days before mortality counts and estimates of reduction in feeding damage are made.

*Diabrotica virgifera virgifera* Leconte, 3rd instar western corn rootworm (WCR)

One cc of fine talc is placed in a 30 mL wide-mouth screw-top glass jar. One mL of the appropriate acetone test solution is pipetted onto the talc so as to provide 1.25 mg of active ingredient per jar. The jars are set under a gentle air flow until the acetone is evaporated. The dried talc is loosened, 1 cc of millet seed is added to serve as food for the insects and 25 mL of moist soil is added to each jar. The jar is capped and the contents thoroughly mixed mechanically. Following this, ten 3rd instar rootworms are added to each jar and the jars are loosely capped to allow air exchange for the larvae. The treatments are held for 5 days when mortality counts are made. Missing larvae are presumed dead, since they decompose rapidly and can not be found. The concentrations of active ingredient used in this test correspond approximately to 50 kg/ha.

The tests are rated according to the scale shown below and the data obtained are shown in Tables VIII and IX. When more than one test is conducted, the results are averaged.

RATING SCALE

| Rate | % Mortality |
| --- | --- |
| 0 | no effect |
| 1 | 10–25 |
| 2 | 26–35 |
| 3 | 36–45 |
| 4 | 46–55 |
| 5 | 56–65 |
| 6 | 66–75 |
| 7 | 76–85 |
| 8 | 86–99 |
| 9 | 100 |
| — | not tested |

TABLE VIII

Insecticidal And Acaricidal Evaluation Of Substituted Indole Compounds

| | % Mortality | | | | | |
| --- | --- | --- | --- | --- | --- | --- |
| | SAW | | SCR | | LH | |
| Compound (Ex. No.) | (1000 ppm) | (300 ppm) | (50 ppm) | TSM (300 ppm) | (300 ppm) | TBW (100 ppm) |
| 2 | 0 | — | 0 | 8 | 0 | 0 |
| 4 | 0 | — | 9 | 0 | — | — |
| 5 | 9 | — | 0 | 0 | — | 9 |
| 9 | 0 | — | 0 | 0 | — | — |
| 10 | 9 | — | 9 | 0 | — | — |
| 11 | — | 9 | — | 9 | — | 9 |
| 12 | — | — | — | 0 | — | — |
| 13 | — | 9 | 0 | 8 | 7 | 9 |
| 14A | — | 9 | 7 | 8 | 9 | 9 |
| 14B | — | 9 | 9 | 6 | 9 | 9 |
| 15A | — | 3 | 4 | 8 | 1 | 0 |
| 15B | 8 | 9 | 9 | 0 | 2 | 1 |
| 16 | — | 9 | 9 | 8 | 9 | — |
| 17 | — | 9 | 9 | 8 | 9 | 9 |
| 18 | — | 2 | 0 | 0 | 0 | 0 |
| 19A | — | 9 | 0 | 0 | 3 | 5 |
| 19B | — | 0 | 0 | 0 | 0 | 0 |
| 20 | — | 7 | 0 | 0 | 0 | 0 |
| 21 | — | 8 | 9 | 5 | 3 | 3 |
| 22 | — | 0 | 0 | 3 | 0 | 1 |
| 23 | — | 0 | 0 | 3 | 0 | 1 |

TABLE IX

Insecticidal And Acaricidal Evaluation Of Substituted Indole Compounds

| | % Mortality | | | | | |
| --- | --- | --- | --- | --- | --- | --- |
| | SAW | | WCR | | LH | |
| Compound (Ex. No.) | (1000 ppm) | (300 ppm) | (50 ppm) | TSM (300 ppm) | (100 ppm) | TBW (100 ppm) |
| 24 | 9 | — | 2 | 8 | — | — |
| 25 | 0 | — | 3 | 7 | — | — |
| 26 | 0 | — | 2 | 5 | — | — |
| 27 | 7 | — | 0 | 9 | — | — |
| 28 | 2 | — | 0 | 0 | — | — |
| 29 | 9 | 9 | 0 | 0 | — | — |
| 30 | 0 | — | 0 | 0 | — | — |
| 31 | 9 | 4 | 0 | 4 | 0 | 0 |
| 33 | 9 | 9 | 5 | 4 | 9 | 0 |
| 34 | 9 | — | 9 | 9 | — | — |
| 35 | 9 | — | 0 | 8 | — | — |
| 37 | 9 | 9 | 0 | 0 | — | — |
| 38 | 8 | 9 | 0 | 0 | — | — |
| 39 | 9 | — | 2 | 3 | — | — |
| 40 | 0 | — | 3 | 0 | — | — |
| 41 | 9 | — | 2 | 0 | — | — |
| 42 | 9 | — | 6 | 0 | 8 | 4 |
| 44 | 9 | — | 0 | 9 | — | — |

TABLE IX-continued

Insecticidal And Acaricidal Evaluation Of Substituted Indole Compounds

| Compound (Ex. No.) | % Mortality | | | | | |
|---|---|---|---|---|---|---|
| | SAW (1000 ppm) | SAW (300 ppm) | WCR (50 ppm) | TSM (300 ppm) | LH (100 ppm) | TBW (100 ppm) |
| 45 | 0 | — | 0 | 0 | — | — |
| 46 | 9 | 9 | 9 | 4 | 9 | 8 |
| 47 | 9 | — | 0 | 9 | — | — |
| 50 | 8 | 3 | 3 | 4 | — | — |
| 51 | 2 | — | 0 | 9 | — | — |
| 52 | 9 | 9 | 6 | 7 | 8 | 0 |
| 53 | 0 | — | 4 | 0 | — | — |
| 54 | 0 | — | 7 | 0 | — | — |
| 55 | 0 | — | 9 | 0 | — | — |
| 56 | 9 | 9 | 8 | 7 | 9 | 0 |
| 57 | 4 | — | 2 | 0 | — | — |
| 58 | 9 | — | 9 | 3 | — | — |
| 59 | 9 | — | 8 | 0 | — | — |
| 60 | 9 | — | 9 | 5 | — | — |
| 62 | 2 | — | 0 | 0 | — | — |
| 63 | 5 | — | 0 | 0 | — | — |
| 64 | 9 | — | 8 | 8 | — | — |
| 65 | 9 | — | 9 | 0 | — | — |
| 66 | 0 | — | 0 | 0 | — | — |
| 68 | 7 | — | 2 | 0 | — | — |
| 69 | 7 | — | 0 | 0 | — | — |
| 71 | 9 | — | 7 | 0 | — | — |
| 75 | 9 | — | 0 | 0 | — | — |
| 78 | 0 | — | 0 | 0 | — | — |

What is claimed is:

1. A method for the control of insect or acarid pests which comprises contacting said pests of their food supply, habitat or breeding grounds with a pesticidally effective amount of a compound formula I

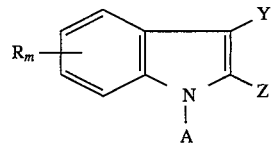

wherein Y and Z are each independently CN or $C_1$ haloalkyl; R is halogen, m is 2 and A is hydrogen.

2. The method of claim 1 wherein $C_1$ haloalkyl is trifluoromethyl and R is chlorine.

3. A method for the protection of growing plants from attack or infestation by insect or acarid pests which comprises applying to the foliage of the plants, or to the soil or water in which they are growing, a pesticidally effective amount of a compound of formula I

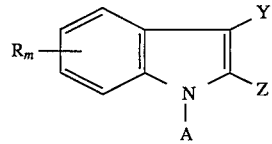

wherein Y, Z, A, R and m are as described in claim 1.

4. The method of claim 3 wherein $C_1$ haloalkyl is trifluoromethyl and R is chlorine.

* * * * *